United States Patent

Hart et al.

[11] Patent Number: 5,246,950
[45] Date of Patent: Sep. 21, 1993

[54] THIOFORMAMIDE DERIVATIVES

[75] Inventors: Terance W. Hart, Brentwood; Bernard Y. J. Vacher, Dagenham; Brian W. Sharp, Hornchurch, all of England

[73] Assignee: Rhone-Poulenc Sante, France

[21] Appl. No.: 501,852

[22] Filed: Mar. 30, 1990

[30] Foreign Application Priority Data

Mar. 31, 1989 [GB] United Kingdom ............... 8907307
Jun. 16, 1989 [GB] United Kingdom ............... 8913862

[51] Int. Cl.$^5$ ..................... A61K 31/44; C07D 213/16
[52] U.S. Cl. ..................... 514/357; 514/336; 514/351; 544/224; 544/238; 544/333; 544/335; 544/336; 544/360; 546/152; 546/174; 546/175; 546/180; 546/263; 546/268; 546/277; 546/278; 546/283; 546/284; 546/300; 546/303; 546/330; 546/331; 546/340; 546/343; 548/204; 548/496; 549/427

[58] Field of Search ............ 546/300, 303, 336, 330, 546/331; 514/351, 357; 544/360

[56] References Cited

FOREIGN PATENT DOCUMENTS 0390693 10/1990 European Pat. Off. ............ 546/300

Primary Examiner—C. Warren Ivy
Assistant Examiner—James H. Turnipseed
Attorney, Agent, or Firm—Morgan & Finnegan

[57] ABSTRACT

Thioformamide derivatives of the formula (I)

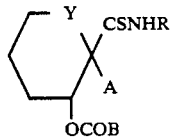

wherein R represents an alkyl group;
  A represents either:
    (1) a phenyl group which is optionally substituted; or
    (2) heteroaromatic group (e.g. pyrid-3-yl, quinolin-3-yl);
  Y represents:
    an ethylene or methylene group or a direct bond; and B represents either:
    a) a phenyl, pyridyl, furyl or thienyl group, each of which may be optionally substituted, or
    b) a straight- or branched-chain alkyl, alkenyl, or cycloalkyl group, each of which may be optionally substituted.

These compounds may be formulated into pharmaceutical preparations and have utility in the treatment of disorders associated with smooth muscle contraction.

8 Claims, No Drawings

THIOFORMAMIDE DERIVATIVES

FIELD OF THE INVENTION

This invention relates to new therapeutically useful thioformamide derivatives, to processes for their preparation and to pharmaceutical compositions containing them.

BACKGROUND OF THE INVENTION

The new thioformamide derivatives of the present invention are those compounds of formula (I), hereinafter depicted wherein:

R represents an alkyl group;
A represents either:
- (1) a phenyl group which is optionally substituted, preferably at the 3 and/or 5 position(s), by a halogen atom or a cyano, nitro, trifluoromethyl, carbamoyl, carboxyl, alkoxycarbonyl or alkylsulphonyl group and which may be further substituted by halogen atom(s), alkyl group(s), aryl-containing group(s) having six to twelve carbon atoms, or substituents which form a fused ring thereon; or
- (2) a heteroaromatic group containing 1 or 2 nitrogen atoms selected from pyrid-3-yl, quinolin-3-yl, isoquinolin-4-yl, pyridazin-4-yl, pyrimidin-5-yl, pyrazin-3-yl, indol-3-yl and thiazol-5-yl, optionally substituted by an alkyl or alkoxy group, or a halogen atom;

Y represents:
an ethylene or methylene group or a direct bond; and

B represents either:
- a) a phenyl, pyridyl, furyl or thienyl group, each of which may be optionally substituted by one or more substituents selected from halogen atoms; hydroxy, alkyl, $C_{2-4}$-alkenyl, alkoxy, phenoxy, tetrahydropyranyloxy, alkanoyl, benzoyl, cyano, nitro, trifluoromethyl, carboxy, amino, (optionally hydroxy)alkylamino, di(optionally hydroxy)alkylamino, trialkylammonio, alkoxycarbonylamino, alkanoylamino, benzoylamino, alkanoyloxy or alkoxycarbonyl groups; or carbamoyl groups (unsubstituted or substituted by one or two alkyl groups in turn optionally substituted by hydroxy groups, or by a straight- or branched chain divalent radical containing from 4 to 6 atoms in the chain and which may contain a further heteroatom (e.g. piperazino- or piperidino-carbonyl)); or
- b) a straight- or branched-chain alkyl group (containing from 1 to 6 carbon atoms), alkenyl group (containing from 2 to 6 carbon atoms) or cycloalkyl group (containing from 3 to 6 carbon atoms), each of which may be optionally substituted by one or more substituents selected from halogen atoms; phenyl, naphthyl, imidazolyl or pyridyl groups (each optionally substituted as in a) above); hydroxy, $C_{2-4}$-alkenyl, alkoxy, phenoxy, tetrahydropyranyloxy, alkanoyl, benzoyl, cyano, nitro, carboxy, amino, (optionally hydroxy)alkylamino, di(optionally hydroxy)alkylamino, trialkylammonio, alkoxycarbonylamino, alkanoylamino, benzoylamino, alkanoyloxy or alkoxycarbonyl groups; or carbamoyl groups (unsubstituted or substituted by one or two alkyl groups in turn optionally substituted by hydroxy groups, or by a straight- or branched chain divalent radical containing from 4 to 6 atoms in the chain and which may contain a further heteroatom (e.g. piperazino- or piperidino-carbonyl), the cycloalkyl group optionally also bearing alkyl or trifluoromethyl groups;

wherein all alkyl groups and moieties, including those in alkoxy, alkoxycarbonyl and alkanoyl groups, can be straight-chain or branched, and, unless otherwise specified, contain one to four carbon atoms; and stereoisomers and salts thereof.

Particularly important classes of compounds of formula (I) exhibit one of more of the following features:
- i) R is a methyl group;
- ii) A is heteroaromatic and is preferably quinolin-3-yl or, more preferably, pyrid-3-yl;
- iii) Y is a methylene group; and
- iv) B is either:
  - a) a pyridyl (preferably pyrid-3 or 4-yl), furyl (preferably furan-2-yl), thienyl (preferably thien-2-yl) or phenyl group each of which may be optionally substituted by one or more groups selected from halogen (preferably fluorine or chlorine) atoms or alkyl, alkoxy, trifluoromethyl, carboxy or dialkylamino groups; or
  - b) an alkyl group (containing 1 to 6 carbon atoms), an alkenyl group (containing 2 to 6 carbon atoms) or cycloalkyl group (containing 3 to 6 carbon atoms) each of which may be optionally substituted by one or more hydroxy, alkoxy, phenoxy, tetrahydropyranyloxy, carboxy, amino, dialkylamino, trialkylammonio, alkoxycarbonyl, alkoxycarbonylamino, alkanoyloxy, N-alkylcarbamoyl, N,N-dialkylcarbamoyl, N'-alkylpiperazinocarbonyl or optionally substituted (preferably by benzoyl or nitro groups) phenyl or imidazolyl (preferably imidazol-1-yl) groups;

the other symbols being as hereinbefore defined, and their stereoisomers and pharmaceutically acceptable salts.

Particularly preferred values for B include phenyl, 2-, 3- or 4-fluorophenyl, 3,4-difluorophenyl, 4-chlorophenyl, 2-methylphenyl, 3- or 4-methoxyphenyl, 3,4,5-trimethoxyphenyl, 2-, 3- or 4-trifluoromethylphenyl, 3,5-bistrifluoromethylphenyl, 2-carboxyphenyl, 4-dimethylaminophenyl, pyrid-3 or 4-yl, furan-2-yl, thien-2-yl, methyl, propyl, t-butyl, benzyl, phenethyl, diphenylmethyl, 1-(3-benzoylphenyl)ethyl, 2-methyl-5-nitroimidazol-1-ylmethyl, hydroxymethyl, methoxymethyl, phenoxymethyl, tetrahydropyran-2-yloxymethyl, cyanomethyl, 2-carboxyethyl, aminomethyl, 1-amino-2-phenylethyl, dimethylaminomethyl, trimethylammoniomethyl, 3-trimethylammoniopropyl, t-butoxycarbonylaminomethyl, acetoxymethyl, 2-methoxycarbonylethyl, 2-(N-methylcarbamoyl)ethyl, 2-(N,N-dimethylcarbamoyl)ethyl, 2-(N'-methylpiperazinocarbonyl)ethyl, 2-phenylethenyl, 1-cyano-2-phenylethenyl, cyclopropyl and 1-phenylcyclopropyl groups.

The presence of a carbonyloxy group on the ring creates an isomeric center in the molecule which in association with the adjacent asymmetric ring carbon atom leads to 4 stereoisomers which, optionally, can be separated into 2 racemic pairs The racemic pair and enantiomers in which the —OCOB and —CSNHR groups are in the trans relationship are preferred and the [1S,2R] enantiomers are particularly preferred.

In certain cases the substituents A, B, and R can also contribute to stereoisomerism. All such forms are also embraced by the present invention.

Particularly important compounds of the present invention include the following:

A (±)-trans-2-Butanoyloxy-N-methyl-1-(pyrid-3-yl)cyclohexanecarbothioamide

B (±)-trans-2-(4-Fluorobenzoyloxy)-N-methyl-1-(pyrid-3-yl)cyclohexanecarbothioamide C (±)-trans-N-Methyl-2-phenylacetoxy-1-(pyrid-3-yl)cyclohexanecarbothioamide D (±)-trans-2-(2-Carboxybenzoyloxy)-N-methyl-1-(pyrid-3-yl)cyclohexanecarbothioamide E (±)-trans-N-Methyl-1-(pyrid-3-yl)-2-succinyloxycyclohexanecarbothioamide F (±)-trans-2-Acetoxy-N-methyl-1-(pyrid-3-yl)cyclohexanecarbothioamide G (±)-trans-2-Benzoyloxy-N-methyl-1-(pyrid-3-yl)cyclohexanecarbothioamide H (±)-trans-N-Methyl-2-(pyrid-3-ylcarbonyloxy)-1-(pyrid-3-yl-)cyclohexanecarbothioamide I (±)-cis-2-Acetoxy-N-methyl-1-(pyrid-3-yl)cyclohexanecarbothioamide J (±)-cis-2-Benzoyloxy-N-methyl-1-(pyrid-3-yl)cyclohexanecarbothioamide K [1S,2R]-trans-2-Benzoyloxy-N-methyl-1-(pyrid-3-yl)cyclohexanecarbothioamide L (±)-trans-N-Methyl-2-(2-methylbenzoyloxy)-1-(pyrid-3-yl)cyclohexanecarbothioamide M (±)-trans-2-(4-Chlorobenzoyloxy)-N-methyl-1-(pyrid-3-yl)cyclohexanecarbothioamide N (±)-trans-2-(3-Fluorobenzoyloxy)-N-methyl-1-(pyrid-3-yl)cyclohexanecarbothioamide O (±)-trans-2-(2-Fluorobenzoyloxy)-N-methyl-1-(pyrid-3-yl)cyclohexanecarbothioamide P (±)-trans-2-(3,4-Difluorobenzoyloxy)-N-methyl-1-(pyrid-3-yl)cyclohexanecarbothioamide Q (±)-trans-N-Methyl-1-(pyrid-3-yl)-2-(2-trifluoromethylbehzoyloxy)cyclohexanecarbothioamide R (±)-trans-N-Methyl-1-(pyrid-3-yl)-2-(3-trifluoromethylbenzoyloxy)cyclohexanecarbothioamide S (±)-trans-N-Methyl-1-(pyrid-3-yl)-2-(4-trifluoromethylbenzoyloxy)cyclohexanecarbothioamide T (±)-trans-2-(3,5-Bistrifluoromethylbenzoyloxy)-N-methyl-1-(pyrid-3-yl)cyclohexanecarbothioamide U (±)-trans-2-(3-Methoxybenzoyloxy)-N-methyl-1-(pyrid-3-yl)cyclohexanecarbothioamide V (±)-trans-2-(4-Dimethylaminobenzoyloxy)-N-methyl-1-(pyrid-3-yl)cyclohexanecarbothioamide W (±)-trans-N-Methyl-1-(pyrid-3-yl)-2-(3,4,5-trimethoxybenzoyloxy)cyclohexanecarbothioamide X (±)-trans-2-(4-Methoxybenzoyloxy)-N-methyl-1-(pyrid-3-yl)cyclohexanecarbothioamide Y (±)-trans-N-Methyl-2-(pyrid-4-ylcarbonyloxy)-1-(pyrid-3-yl)cyclohexanecarbothioamide Z (±)-trans-2-(2-Furoyloxy)-N-methyl-1-(pyrid-3-yl)cyclohexanecarbothioamide AA (±)-trans-N-Methyl-1-(pyrid-3-yl)-2-(thien-2-oyloxy)cyclohexanecarbothioamide AB (±)-cis-2-Benzoyloxy-N-methyl-1-(quinolin-3-yl)cyclohexanecarbothioamide AC (±)-trans-2-Benzoyloxy-N-methyl-1-(quinolin-3-yl)cyclohexanecarbothioamide AD [1R, 2S]-trans-2-Benzoyloxy-N-methyl-1-(pyrid-3-yl)cyclohexanecarbothioamide AE cis/trans-[(2-N-methyl{thiocarbamoyl}-2-{pyrid-3-yl}cyclohexyloxycarbonyl)methyl]trimethylammonium chloride AF (±)-trans-[3-(2-N-methyl{thiocarbamoyl}-2-{pyrid-3-yl}cyclohexyloxycarbonyl)propyl]-trimethylammonium chloride AG (±)-trans-N-Methyl-2-[(2-methyl-5-nitroimidazol-1-yl-)acetoxy]-1-(pyrid-3-yl)cyclohexanecarbothioamide AH (±)-trans-2-Acetoxyacetoxy-N-methyl-1-(pyrid-3-yl)cyclohexanecarbothioamide AI (±)-trans-N-Methyl-2-(1-phenylcyclopropylcarbonyloxy)-1-(pyrid-3-yl)cyclohexanecarbothioamide AJ (±)-trans-2-Diphenylacetoxy-N-methyl-1-(pyrid-3-yl)cyclohexanecarbothioamide AK (±)-trans-N-Methyl-2-(3-phenylpropenoyloxy)-1-(pyrid-3-yl)cyclohexanecarbothioamide AL N,N-Dimethylglycine (±)-trans-[N-methyl(thiocarbamoyl)]-2-(pyrid-3-yl)cyclohexyl ester AM (±)-trans-2-[2-(3-benzoylphenyl)propanoyloxy]N-methyl-1-(pyrid-3-yl)cyclohexanecarbothioamide AN (±)-trans-N-Methyl-1-(pyrid-3-yl)-2-trimethylacetoxycyclohexanecarbothioamide AO (±)-trans-2-(3-Methoxycarbonylpropanoyloxy)-N-methyl-1-(pyrid-3-yl)cyclohexanecarbothioamide AP (±)-trans-2-Cyclopropanoyloxy-N-methyl-1-(pyrid-3-yl)cyclohexanecarbothioamide AQ (±)-cis-2-Acetoxy-N-methyl-1-(quinolin-3-yl)cyclohexanecarbothioamide AR (±)-trans-2-Acetoxy-N-methyl-1-(quinolin-3-yl)cyclohexanecarbothioamide AS (±)-trans-2-(2-Cyano-3-phenylpropenoyloxy)-N-methyl-1-(pyrid-3-yl)cyclohexanecarbothioamide AT (±)-trans-2-Methoxyacetoxy-N-methyl-1-(pyrid-3-yl)cyclohexanecarbothioamide AU (±)-trans-N-Methyl-2-phenoxyacetoxy-1-(pyrid-3-yl)cyclohexanecarbothioamide AV (±)-trans-2-Cyanoacetoxy-N-methyl-1-(pyrid-3-yl)cyclohexanecarbothioamide AW (±)-trans-N-Methyl-2-[3-(N-methylcarbamoyl)-propanoyloxy]-1-(pyrid-3-yl)cyclohexanecarbothioamide AX (±)-trans-N-Methyl-2-[3-(4-methylpiperazin-1-ylcarbonyl)propanoyloxy]-1-(pyrid-3-yl)cyclohexanecarbothioamide AY (±)-trans-N-Methyl-1-(pyrid-3-yl)-2-(tetrahydropyran-2-yloxy)acetoxycyclohexanecarbothioamide AZ L-Phenylalanine (±)-trans-[N-methyl(thiocarbamoyl)]-2-(pyrid-3-yl)cyclohexyl ester BA Glycine (±)-trans-[N-methyl(thiocarbamoyl)]-2-(pyrid-3-yl)cyclohexyl ester BB (±)-trans-2-Hydroxyacetoxy-N-methyl-1-(pyrid-3-yl)cyclohexanecarbothioamide BC (±)-trans-2-[3-(N,N-Dimethylcarbamoyl)-propanoyloxy]-N-methyl-1-(pyrid-3-yl)cyclohexanecarbothioamide BD (±)-trans-N-Methyl-2-(3-phenylpropanoyloxy)-1-(pyrid-3-yl)cyclohexanecarbothioamide BE (±)-trans-2-t-Butoxycarbonylaminoacetoxy-N-methyl-1-(pyrid-3-yl)cyclohexanecarbothioamide as well as their stereoisomeric forms and pharmaceutically acceptable salts thereof Letters A to BE are allocated to compounds for ease of reference in other parts of the specification.

The compounds have valuable pharmacological properties, in particular properties which are indicative of utility in the treatment and/or prophylaxis of disorders associated with:

(1) vascular smooth muscle contraction including hypertension and other cardiovascular disorders such as congestive heart failure, and conditions associated with tissue ischaemia such as angina, peripheral vascular disease and cerebrovascular disease;

(2) respiratory smooth muscle contraction including reversible airways obstruction and asthma;

(3) contraction of smooth muscle of gastrointestinal tract, urinary bladder and uterus, including peptic ulcers, irritable bowel syndrome and diverticular disease; and premature labour.

The compounds also have utility in the inhibition of head hair loss associated with male pattern baldness, by topical application.

For example, compounds of general formula (I) were submitted to:

Vaso-relaxant Activity Tests

The test methods used were adapted from those described by Winslow et al [Eur.J.Pharmacol., 131, 219-228 (1986)] and Karaki [J.Pharmacol Methods, 18, 1-21 (1987)] for differentiating vaso-relaxant activity.

Test A: Activity against contractions induced by low $K^+$ concentrations in the isolated rat aorta Thoracic aorta was removed from rats and transverse strips, denuded of endothelium, were suspended in a bath containing Krebs solution. The tension was recorded and a contraction induced by addition of 20 mM $K^+$ (potassium ion) to the bathing solution. The test compound was added to the bath as a solution in increasing cumulative concentration. The concentration in the bathing solution of the test compound which reduced the $K^+$-induced contraction by 90% was determined and expressed in $\mu M$ as the effective concentration ($EC_{90}$), given in Table 1.

TABLE 1

| Compound | $EC_{90}$ |
|---|---|
| A | 0.001 |
| B | 0.0003 |
| C | 0.01 |
| D | 30 |
| E | 1. |
| F | 0.1 |
| G | 0.0001 |
| H | 0.001 |
| I | 10 |
| J | 10-30 |
| K | 0.0003 |
| L | 0.0002 |
| M | 0.0002 |
| N | 0.0005 |
| O | 0.001 |
| P | 0.0003 |
| Q | 0.001 |
| R | 0.003 |
| S | 0.001 |
| T | 0.03 |
| U | 0.07 |
| V | 1-3 |
| W | 0.07 |
| X | 0.02 |
| Y | 0.007 |
| Z | 0.03 |
| AA | 0.01 |
| AB | 5 |
| AC | 0.007 |
| AD | 3 |
| AE | 30 |
| AH | 0.1 |
| AK | 0.3 |
| AL | 0.02 |

TABLE 1-continued

| Compound | $EC_{90}$ |
|---|---|
| AM | 0.03 |
| AN | 0.02 |
| AO | 0.03 |
| AP | 0.01 |
| AQ | 10 |
| AR | 0.01 |
| AS | 0.02 |
| AT | 0.03 |
| AU | 0.04 |
| AV | 3 |
| AW | 0.1 |
| AX | 10 |
| AY | 0.1 |
| AZ | 0.03 |
| BA | 0.1 |
| BB | 0.03 |
| BC | 0.3 |
| BD | 0.0003 |
| BE | 0.01 |

Test B: Activity against contractions induced by high $K^+$ concentrations in isolated rat aorta The test method was as in Test A with the exception that concentrations were induced by addition of 60 mM $K^+$ to the bathing solution. The cumulative addition of the solutions of the test compound was conducted and the concentration in the bath reducing the $K^+$-induced contraction by 90% was found and expressed as the $EC_{90}$. For each compound tested it was greater than 30 $\mu M$.

The compounds of general formula (I) can be prepared by the application and adaptation of known methods, for example as hereinafter identified. By the term "known methods" as used in this specification is meant methods heretofore used or described in the literature.

According to a feature of the present invention, the compounds of general formula (I), as hereinbefore defined, may be prepared by the reaction of a compound of general formula (II), wherein A, Y and R are as hereinbefore defined, with a compound of general formula:

BCOOH  (III)

or an acid halide, preferably chloride, or reactive acid anhydride thereof, wherein B is as hereinbefore defined.

Reaction with acid is generally carried out in an inert, organic solvent, optionally in the presence of a proton acceptor and of a coupling agent, such as dicyclohexylcarbodiimide or carbonyldiimidazole.

Reaction with an acid halide is also generally carried out in an inert solvent, optionally in the presence of a proton acceptor.

Reaction with an anhydride is carried out under similar conditions to that with an acid halide.

Compounds of formula (III) may be generated in situ from salts thereof.

Typical solvents include acetonitrile, pyridine, dichloromethane, chloroform, acetone, dimethylformamide, water and mixtures thereof.

Typial proton acceptors may be organic bases such as triethylamine or, preferably, 4-dimethylaminopyridine or inorganic bases such as sodium bicarbonate.

Reaction temperatures for all three reaction variations typically vary from $-30°$ C. to reflux.

The compounds of general formula (II), wherein A, Y and R are as hereinbefore defined, may be prepared by the reduction of the corresponding compounds of general formula (IV).

The reduction can be carried out in an inert organic solvent such as methanol or dimethylsulphoxide, or a mixture of these solvents at a temperature from −20° C. to +50° C., using an alkali metal borohydride, e.g. sodium borohydride.

Alternatively the reduction can be carried out using an aluminium alkoxide (e.g. the isopropoxide) in an alcoholic solvent (e.g. isopropanol) at temperatures up to reflux.

Both reactions produce both the cis and trans compounds.

Compounds of general formula (IV), wherein A, Y and R are as hereinbefore defined may be prepared by the reaction of a compound of general formula (V), wherein A and Y are as hereinbefore defined, with an isothiocyanate of the general formula:

$$R-N=C=S \qquad (VI)$$

wherein R is as hereinbefore defined. The reaction is generally carried out in an anhydrous inert organic solvent such as tetrahydrofuran, dimethylformamide or hexamethylphosphoramide, or a mixture of these solvents, at a temperature from −80° C. to +50° C., in the presence of an inorganic base such as potassium tert.-butoxide, or an organo-lithium derivative such as n-butyllithium, or of sodium hydride.

A stereoselective synthesis of the compounds of formula (IV) may be carried out by reaction of a mixture of enantiomers of general formula (V) with a chiral auxiliary agent, before being reacted with a compound of general formula (VI) as hereinbefore described followed by the removal of the chiral auxiliary agent.

The chiral auxiliary agent is typically a compound of formula:

$$Q-NH_2 \qquad (VII)$$

wherein Q is a chiral group, for example asymmetrically substituted pyrollidino or asymmetrically substituted methyl.

Preferred pyrollidines include 1-amino-2-methoxymethyl pyrollidine.

(Asymmetric methyl)amines are preferred reagents.

The preferred (asymmetric methyl)amines have two substituents on the methyl group. Any alkyl substituents may be optionally substituted. All substituents are preferably not alkyl and it is particularly preferred that one is an optionally substituted aromatic or heteroaromatic group. Particularly preferred (asymmetric methyl)amines include 1-phenylethylamine, 1-(1-naphthyl)ethylamine and 1-(pyrid-3-yl)ethylamine.

Reaction of a compound of formula (V) with a compound of formula (VII) produces a compound of formula (VIII). Reaction of this with a compound of formula (VI) preferentially produces one enantiomer of compound of formula (IX). The chiral compound of formula (IV) can be produced therefrom by hydrolysis.

Compounds of formula (V), wherein A is as hereinbefore defined and Y is a methylene or ethylene group, can be made via a dehydrobromination/rearrangement reaction of compounds of formula (X), wherein A is as defined above and $Y^1$ is methylene or ethylene. This may be initiated by a bromide extracting agent such as a silver salt (e.g. silver perchlorate) and carried out in an inert anhydrous solvent (for example an ether such as tetrahydrofuran).

Compounds of formula (X), wherein A and $Y^1$ are as defined above, can be made by the addition of hypobromous acid across the double bond of compounds of formula (XI), wherein A and $Y^1$ are as defined above. This may be done by reaction with a brominating agent (e.g. 1,3-dibromo-5,5-dimethylhydantoin) in an aqueous acidic medium, optionally in the presence of a cosolvent.

Compounds of formula (XI), wherein A and $Y^1$ are as defined above, can be made via a coupling reaction between a phosphorane of formula (XII) (typically made in situ by the reaction of a compound of formula (XIII), wherein $Y^1$ is as defined above and $R^1$ and Z are conventional groups present in a Wittig reagent and its phosphonium salt precursor [e.g. phenyl and bromine respectively] with a strong base, such as potassium t-butoxide, in an anhydrous solvent, such as tetrahydrofuran, preferably under an inert atmosphere) and a compound of formula:

$$A-CHO \qquad (XIV)$$

wherein A is as defined above.

Alternatively compounds of formula (V), wherein Y is ethylene, methylene or a direct bond and A is as hereinbefore defined, can be made by the removal of methanol from compounds of formula (XV), wherein A and Y are as defined above. This is typically carried out in the presence of a strongly acidic agent (e.g. phosphorus pentoxide or sulphuric acid), optionally in a solvent (such as toluene) and at elevated temperature, followed by hydrolysis of the intermediate enol ether.

Compounds of formula (XV) can be made by reaction of a compound of formula:

$$A-Z \qquad (XVI)$$

wherein A is as defined above and $Z^1$ is a halogen, preferably bromine or chlorine atom, in the presence of a strong base, such as an alkyl lithium (e.g. butyllithium), with a compound of formula (XVII), wherein Y is as defined above, in an inert solvent such as an ether (e.g. diethyl ether) or a hydrocarbon (e.g. toluene).

Alternatively, compounds of general formula (IV), wherein A and Y are as hereinbefore defined and R is methyl, can be prepared from compounds of general formula (XVIII), wherein A and Y are as defined above and $R^2$ is an alkyl group of 1 to 4 carbon atoms or a benzyl or carboxymethyl radical, by reaction with methylamine. The reaction is generally carried out with an excess of amine, without a solvent or in an inert organic solvent such as an ether (e.g. tetrahydrofuran) an aromatic hydrocarbon or an alcohol or a mixture of these solvents at a temperature from room temperature to 130° C., optionally under pressure, and the amine may be added in an alcoholic solution, preferably ethanol.

It may be advantageous for the thiol formed during the reaction to be fixed in the form of a heavy metal salt using a thiol acceptor such as mercuric chloride.

Compounds of formula (XVIII), wherein Y, A and $R^2$ are as hereinbefore defined may be prepared by the reaction of compounds of formula (V), wherein Y and A are as hereinbefore defined, with carbon disulphide followed by reaction with a compound of formula:

$$R^2-Z^2 \qquad (XI)$$

wherein $R^2$ is as hereinbefore defined and $Z^2$ is halogen, preferably chlorine, bromine or iodine, or a readily displaceable ester group such as methanesulphonyloxy or 4-toluenesulphonyloxy. The reaction is generally carried out in an anhydrous inert organic solvent such as tetrahydrofuran, to which hexamethylphosphoramide may be added, at a temperature from $-80°$ C. to $+50°$ C. in the presence of an organic base such as potassium tert.-butoxide, or an organo-lithium derivative such as butyllithium, or sodium hydride.

Compounds of formulae (III), (VI), (VII), (XIII), (XIV), (XVI), (XVII) and (XIX) can be made by application or adaptation of known methods or are readily available.

It will be understood that it may be desirable to change one or more of the substituents on the alkyl or aryl groups at an appropriate stage during the synthesis of the compounds of the invention. For example, the compounds of general formula (I) wherein A represents a phenyl group substituted by a carbamoyl group may be alternatively prepared from the corresponding compounds of general formula (I) wherein A represents a phenyl group substituted by a cyano group by the application or adaptation of known methods for such conversion.

Similarly, compounds of formula (I) wherein B contains an alkoxycarbonyl group may h=made from the corresponding acids by esterification in a similar manner to that used for the reaction between compounds of formulae (II) and (III); compounds wherein B contains an amino group may be prepared from the corresponding N-t-butoxycarbonyl compound by hydrolysis using, for example, trifluoroacetic acid; compounds wherein B contains a carbamoyl group may be prepared from the corresponding acid by reaction with the appropriate amine in the presence of a suitable coupling agent, such as carbonyldiimidazole; and compounds wherein B contains a hydroxy group may be prepared by hydrolysis of the corresponding tetrahydropyran-2-yloxy compound, for example with aqueous acetic acid.

It is to be understood that the conversion, for example by known methods, of one compound of general formula (I) into another compound of formula (I) constitutes a feature of the present invention.

By the term "pharmaceutically acceptable salts" as used in this specification is meant salts the anions or cations of which are relatively innocuous to the animal organism when used in therapeutic doses so the the beneficial pharmaceutical properties of the parent compounds of general formula (I) capable of forming salts are not vitiated by side-effects ascribable to those anions or cations.

It is to be understood that, where in this specification reference is made to compounds of formula (I), it is intended to refer also, where the context so permits, to their pharmaceutically acceptable salts.

Suitable acid addition salts for use in pharmaceuticals may by selected from salts derived from inorganic acids, for example hydrochlorides, hydrobromides, phosphates, sulphates and nitrates, and organic acids, for example oxalates, lactates, tartrates, acetates, salicylates, citrates, propionates, succinates, fumarates, maleates, methylene-bis-$\beta$-hydroxynaphthoates, gentisates and di-p-toluoyltartrates.

Suitable salts with bases include alkali metal (e.g. sodium and potassium), alkaline earth metal (e.g. calcium and magnesium), ammonium and amine (e.g. di-ethanolamine, triethanolamine, octylamine, morpholine and dioctylmethylamine) salts.

As well as being useful in themselves as active compounds, salts of the compounds of general formula (I) capable of forming salts with acids or bases are useful for the purposes of purification of the parent compounds of general formula (I), for example by exploitation of the solubility differences between the salts and the parent compounds, by techniques well known to those skilled in the art.

The thioformamide derivatives of general formula (I) obtained by the aforedescribed processes can be purified by the usual physical methods, in particular crystallisation and chromatography, especially to resolve mixtures of enantiomers using a chiral column.

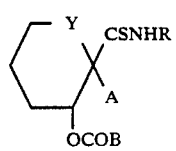
(I)

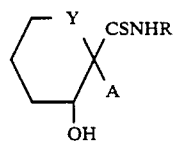
(II)

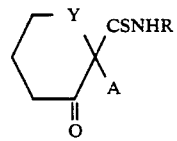
(IV)

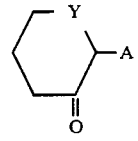
(V)

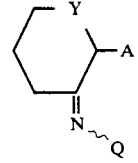
(VIII)

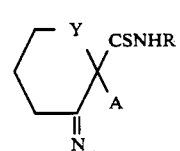
(IX)

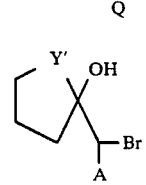
(X)

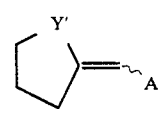
(XI)

-continued

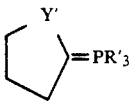 (XII)

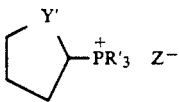 (XIII)

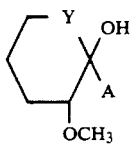 (XV)

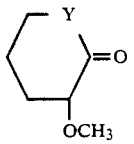 (XVII)

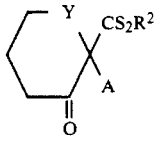 (XVIII)

EXAMPLES

The following Examples illustrate the preparation of compounds according to the present invention.

All N.M.R spectra were recorded at 200 MHz. The chemical shifts are expressed in ppm relative to tetramethylsilane. Abbreviations in the text have the following significances:

s=singlet, d=doublet, dd=doublet of doublets, ddd=doublet of doublets of doublets, dt=doublet of triplets, m=multiplet, c=unresolved complex peak, br=broad signal.

The expression "m/z" indicates the peak assigned to the molecular ion in the mass spectrum.

EXAMPLE 1

Compound A

A solution of (±)-trans-N-methyl-2-hydroxy-1-(pyrid-3-yl)cyclohexanecarbothioamide (1.5 g, 6.0 mmol), 4-dimethylaminopyridine (300 mg) and butyric anhydride (2.84 g, 18 mmol) in pyridine (15 ml) was stirred for 48 hours at 20° C. The solution was concentrated in vacuo and the residue recrystallized from cyclohexane to give (±)-trans-2-butanoyloxy-N-methyl-1-(pyrid-3-yl)cyclohexanecarbothioamide, as a white solid, (1.5 g, 4.7 mmol), m.p. 141°-143° C.;

[Found: C, 63.5; H, 7.5; N, 8.6; S, 9.9%

Calculated for $C_{17}H_{24}N_2O_2S$; C, 63.7; H, 7.6; N, 8.7; S, 10.0%].

EXAMPLE 2

Compound B

A suspension of (±)-trans-N-methyl-2-hydroxy-1-(pyrid-3-yl)cyclohexanecarbothioamide(0.5 g, 2 mmol), 4-fluorobenzoic acid (0.56 g, 4 mmol), dicyclohexylcarbodiimide (0.83 g, 4 mmol) and 4-dimethylaminopyridine (50 mg) in acetonitrile (20 ml) was stirred for 18 hours at 20° C. The mixture was then filtered through diatomaceous earth under vacuum and the filtrate concentrated in vacuo to afford a residue which was dissolved in dichloromethane (20 ml), washed with aqueous sodium carbonate solution (1M, 2×20 ml) and dried over magnesium sulphate. Concentration in vacuo afforded a crude solid which was purified by medium pressure liquid chromatography (flash chromatography), eluting with a mixture (97.5:2.5) of chloroform and methanol over silica gel to give (±)-trans-2-(4-fluorobenzoyloxy)-N-methyl-1-(pyrid-3-yl)cyclohexanecarbothioamide, as a white solid, (0.45 g, 1.2 mmol), m.p. 199°-201° C.;

[Found C, 64.1; H, 5.8; N, 7.4; S, 8.3%.

Calculated for C C, 64.5; H, 5.7; N, 7.5; S, 8.6%].

EXAMPLE 3

Compound C

A suspension of (±)-trans-N-methyl-2-hydroxy-1-(pyrid-3-yl)cyclohexanecarbothioamide (0.50 g, 2 mmol) in acetonitrile (5 ml) was treated sequentially with phenylacetic acid (0.32 g, 2.4 mmol), dicyclohexylcarbodiimide (0.62 g, 3 mmol) and 4-dimethylaminopyridine (50 mg) at 20° C. After 21 hours at 20° C. the reaction mixture was filtered through diatomaceous earth under vacuum and the filtrate concentrated in vacuo. The residue was dissolved in dichloromethane (20 ml) and washed with hydrochloric acid (0.25M, 2×20 ml). The organic layer was then separated, washed with aqueous saturated sodium bicarbonate solution and dried over magnesium sulphate. After concentration of the organic solution in vacuo the resulting solid was recrystallized from ethyl acetate to afford (±)-trans-N-methyl-2-phenylacetoxy-1-(pyrid-3-yl)cyclohexanecarbothioamide, as a white solid, (0.35 g, 9.5 mmol), m.p. 171°-174° C.;

[Found: C, 68.1; H, 6.6; N, 7.6; S, 8.5%

Calculated for $C_{21}H_{24}N_2O_2S$; C, 68.5; H, 6.6; N, 7.6; S, 8.7%].

EXAMPLE 4

Compound D

A solution of (±)-trans-N-methyl-2-hydroxy-1-(pyrid-3-yl)cyclohexanecarbothioamide (0.25 g, 1 mmol), 4-dimethylaminopyridine (50 mg) and phthalic anhydride (0.44 g, 3 mmol) in pyridine (2.5 ml) was stirred at 20° C. for 8 hours and then left standing at 20° C. for 3 weeks. Water (2 ml) was then added and the mixture refluxed for 3 hours and then concentrated in vacuo. The residue was treated with water (10 ml) to precipitate a solid which was filtered off and recrystallized from ethylacetate to give (±)-trans-2-(2-carboxybenzoyloxy)-N-methyl-1-(pyrid-3-yl)cyclohexanecarbothioamide, as a white solid, (0.17 g, 0.43 mmol), m.p. 199°-201° C.; [Found: C, 62.9; H, 5.6; N, 6.7; S, 7.6%

Calculated for $C_{21}H_{22}N_2O_4S$: S:- C, 63.3; H, 5.6; N, 7.0; S, 8.0%].

EXAMPLE 5

Compound E

A solution of (±)-trans-N-methyl-2-hydroxy-1-(3-pyridyl)cyclohexanecarbothioamide (0.25 g, 1 mmol), 4-dimethylaminopyridine (50 mg) and succinic anhydride (0.3 g, 3 mmol) in pyridine (25 ml) was sonicated at 20° C. for 6.5 hours. Water (1 ml) was then added and the mixture was sonicated for a further 2 hours at 20° C. and then heated at reflux for 1 hour. The mixture was concentrated in vacuo and then treated with water (10 ml). The precipitated solid was filtered off and recrystallized from ethyl acetate to aford (±)-trans-N-methyl-1-(pyrid-3-yl)-2-succinyloxycyclohexanecarbothioamide, (0.2 g, 0.57 ml), m.p. 184°-186° C.;

[Found: C, 57.9, H, 6.3; N, 7.9%
Calculated for C C, 58.3, H, 6.3; N, 8.0%].

EXAMPLE 6

Compound F

A solution of (±)-trans-N-methyl-2-hydroxy-1-(3-pyridyl)cyclohexanecarbothioamide (2.5 g, 10 mmol) and 4-dimethylaminopyridine (0.1 g) in pyridine (30 ml) was treated with acetic anhydride (3.06 g, 30 mml) at 20° C. After 3 hours at 20° C. the solution was concentrated in vacuo and the residue recrystallized from ethyl acetate to afford (±)-trans-2-acetoxy-N-methyl-1-(pyrid-3-yl)cyclohexanecarbothioamide, as a white solid, (2.12 g, 7.2 mmol), m.p. 192°-194° C.;

[Found: C, 62.0; H, 6.8; N, 9.5; S, 10.9%
Calculated for C C, 61.6; H, 6.9; N, 9.6; S, 11.0%].

EXAMPLE 7

Compound G

A solution of (±)-trans-N-methyl-2-hydroxy-1-(3-pyridyl)cyclohexanecarbothioamide (1.0 g, 4.0 mmol) and 4-dimethylaminopyridine (480 mg, 4.0 mmol) in pyridine (10 ml) was treated with benzoyl chloride (0.62 g, 4.4 mmol) dropwise over 2 minutes at 10° C. The reaction mixture was then stirred at 20° C. for 48 hours. After partitioning between ethyl acetate (30 ml) and sodium hydroxide (1M, 20 ml) the organic layer was washed with brine (10 ml), dried over sodium sulphate and then concentrated in vacuo to afford a crude oil which was recrystallized from a mixture of ethyl acetate and methanol (9:1) (10 ml) to give (±)-trans-2-benzoyloxy-N-methyl-1-(pyrid-3-yl)cyclohexanecarbothioamide, as a white solid, (0.8 g, 2.25 mmol), m.p. 211°-213° C.;

[N.M.R. (CDCl$_3$): 1.46-1.76 (c, 4H), 1.88-2.12 (c, 2H), 2.32-2.58 (c, 2H), 2.70-2.88 (m, 1H), 3.05 (d, 3H), 6.39 (dd, 1H), 7.2-7.42 (c, 4H), 7.42-7.56 (m, 1H), 7.72-7.84 (m, 2H), 7.96-8.20 (c, 2H), 8.41 (dd, 1H), 8.74 (d, 1H)

[Found: C, 67.7; H, 6.3; N, 7.9; S, 9.0%
Calculated for C$_{20}$H$_{22}$N$_2$O$_2$S: C,67.8; H, 6.3; N, 7.9; S, 9.0%].

EXAMPLE 8

Compound H

A mixture of (±)-trans-N-methyl-2-hydroxy-1-(pyrid-3-yl)cyclohexanecarbothioamide (0.5 g, 2 mmol), 4-dimethylaminopyridine (488 mg, 4.0 mmol), and nicotinyl chloride hydrochloride (392 mg, 2.2 mmol) in pyridine (5 ml) was sonicated for 8 hours at 30° C. and then allowed to stand at 20° C. for 20 hours. The mixture was partitioned between sodium hydroxide solution (0.5M, 30 ml) and dichloromethane (10 ml). The aqueous layer was extracted with dichloromethane (2×10 ml) and the combined organics extracts were washed successively with water (10 ml) and saturated brine solution (10 ml) and dried over sodium sulphate. Concentration in vacuo afforded a crude oil which was recrystallized from ethyl acetate to give (±)-trans-N-methyl-2-(pyrid-3-ylcarbonyloxy)-1-(pyrid-3-yl)cy-clohexanecarbothioamide, as a white solid, (0.39 g, 1.1 mmol), m.p. 192°-194 ° C.;

[Found: C, 64.1; H, 5.9; N, 11.8%
Calculated for C C, 64.2; H, 6.0; N, 11.8%].

EXAMPLE 9

Compound I

A solution of (±)-cis-N-methyl-2-hydroxy-1-(pyrid-3-yl)cyclohexanecarbothioamide (1.25 g, 5 mmol), 4-dimelhylaminopyridine 0.1 g) and acetic anhydride (1.5 g, 15 mmol) in pyridine (15 ml) was stirred at 20° C. for 3 hours. The solution was concentrated in vacuo and the crude product purified by medium pressure liquid chromatography over silica gel, eluting with a 97.5:2.5 mixture of chloroform and methanol to give (±)-cis-2-acetoxy-N-methyl-1-(pyrid-3-yl)cyclohexanecarbothioamide, as a white solid, (0.58 g, 2 mmol), m.p. 169°-171° C.;

[Found: C, 61.6; H, 6.9; N, 9.5; S, 10.8%
Calculated for C$_{15}$H$_{20}$N$_2$O$_2$S. C, 61.6; H, 6.9; N, 9.6; S, 11.0%].

EXAMPLE 10

Compound J

A solution of (±)-cis-N-methyl-2-hydroxy-1-(pyrid-3-yl)cyclohexanecarbothioamide (0.5 g, 2 mmol), benzoyl chloride (0.31 g, 2.2 mmol) and 4-dimethylaminopyridine (0.26 g, 2.2 mmol) in pyridine (10 ml) was stirred at 20° C. for 2 days. After concentration in vacuo the residue was dissolved in dichloromethane (10 ml), washed successively with aqueous sodium carbonate solution (1M, 2×20 ml), water (2×20 ml) and brine solution (20 ml), and then dried over magnesium sulphate. Concentration afforded a crude product which was recrystallized from ethyl acetate to give (±)-cis-2-benzoyloxy-N-methyl-1-(pyrid-3-yl)cyclohexanecarbothioamide, as a white solid, (0.53 g, 1.5 mmol), m.p 196°-198° C.;

[Found: C, 67.4; H, 6.2; N, 7.8%
Calculated for C$_{20}$H$_{22}$N$_2$O$_2$S, C, 67.8; H, 6.3; N, 7.9%].

EXAMPLE 11

Compounds K and AD i) To a solution of [1S,2R]-trans-2-hydroxy-N-methyl-1-(3-pyridyl)cyclohexanecarbothioamide (22.50 g, 90 mmol) in a mixture of anhydrous pyridine (75 ml) and dry dichlomethane (225 ml) at 20° C. was added 4-dimethylaminopyridine (12.2 g, 100 mmol). Benzoyl chloride (15.8 g, 100 mmol) was then added dropwise over 45 minutes with the internal temperature rising to 38° C. The reaction mixture was then stirred at 20° C. for 21 hours. After concentration in vacuo (50° C.; 0.01 mmHg), the residue was dissolved in dichloromethane (250 ml) and washed sucessively with water (50 ml) saturated aqueous sodium carbonate solution (50 ml) and saturated brine (50 ml). After concentration in vacuo (30° C.; 14 mmHg), the residue was extracted with boiling diethyl ether (300 ml). After concentration the residue was recrystallized from the minimum volume of acetonitrile to give [1S,2R]-trans-2-benzoyloxy-N-methyl-1-(pyrid-3-yl)cyclohexanecarbothioamide, as a white solid, (21.36 g, 60.3 mmol), m.p. 174°-175° C.;

[N.M.R. (CDCl$_3$): 1.45-1.55 (m, 2H), 1.55-1.65 (m, 2H), 1.85-1.95 (m, 1H), 2.28-2.37 (m, 1H), 2.45-2.53 (m, 1H), 2.98 (d, 3H), 6.36-6.48 (dd, 1H), 7.20-7.25 (m, 1H), 7.30–7.35 (m, 2H), 7.43–7.52 (m, 2H), 7.74–7.78 (m, 2H), 8.01–8.04 (m, 1H), 8.41–8.43 (dd, 1H), 8.83–8.85 (m, 1H)
Found: C, 68.0; H, 6.2; N, 7.9; S, 9.3%
Calculated for $C_{20}H_{22}N_2O_2S$: C, 67.8; H, 6.3%; N, 7.9; S,9.0% $[\alpha]_D^{25} = -138°$ (c=1.0, $CHCl_3$)].

ii) By proceeding in a similar manner, but replacing the [1S, 2R] alcohol by the [1R, 2S] alcohol, there was prepared [1R,2S]-trans-2-benzoyloxy-N-methyl-1-(pyrid-3-yl)cyclohexanecarbothioamide, as a white solid, m.p. 171°–173° C.

EXAMPLE 12

Compound L to X

By proceeding as in Example 7, but replacing the benzoyl chloride by the appropriate acyl chloride, there were prepared:

i) (±)-trans-N-methyl-2-(2-methylbenzoyloxy)-1-(pyrid-3-yl)cyclohexanecarbothioamide, as a white solid, m.p. 180°–184° C.;

ii) (±)-trans-2-(4-chlorobenzoyloxy)-N-methyl-1-(pyrid-3-yl)cyclohexanecarbothioamide, an off white powder, m.p. 201°–202° C.;

iii) (±)-trans-2-(3-fluorobenzoyloxy)-N-methyl-1-(pyrid-3-yl)cyclohexanecarbothioamide, an off white powder, m.p. 195°–196° C.;

iv) (±)-trans-2-(2-fluorobenzoyloxy)-N-methyl-1-pyrid-3-yl)cyclohexanecarbothioamide, a white solid, m.p. 160°–162° C.;

v) (±)-trans-2-(3,4-difluorobenzoyloxy)-N-methyl-1-(pyrid-3-yl)cyclohexanecarbothioamide, a white solid, m.p. 197°–199° C.;

vi) (±)-trans-N-methyl-1-(pyrid-3-yl)-2-(2-trifluoromethylbenzoyloxy)cyclohexanecarbothioamide, a white crystalline solid, m.p. 209°–210° C.;

vii) (±)-trans-N-methyl-1-(pyrid-3-yl)-2-(3-trifluoromethylbenzoyloxy)cyclohexanecarbothioamide, a white solid, m.p. 194°–196° C.;

viii) (±)-trans-N-methyl-1-(pyrid-3-yl)-2-(4-trifluoromethylbenzoyloxy)cyclohexanecarbothioamide, a white crystalline solid, m.p. 212°–213° C.

ix) (±)-trans-2-(3,5-bistrifluoromethylbenzoyloxy)-N-methyl-1-(pyrid-3-yl)cyclohexanecarbothioamide, a white crystalline solid, m.p. 196°–197° C.;

x) (±)-trans-2-(3-methoxybenzoyloxy)-N-methyl-1-(pyrid-3-yl)cyclohexanecarbothioamide, an off white solid, m.p. 197°–198° C.;

xi) (±)-trans-2-(4-dimethylaminobenzoyloxy)-N-methyl-1-(pyrid-3-yl)cyclohexanecarbothioamide, cream needles, m.p. 236°–238° C.;

xii) (±)-trans-N-methyl-1-(pyrid-3-yl)-2-(3,4,5-trimethoxybenzoyloxy)cyclohexanecarbothioamide, a white solid, m.p. 225°–232° C.; and xiii) (±)-trans-2-(4-methoxybenzoyloxy)-N-methyl-1-(pyrid-3-yl)cyclohexanecarbothioamide, a white solid, m.p. 215°–217° C.

EXAMPLE 13

Compounds Z, AA, AE to AG, AI to AM, AP, AT to AV and BD

By proceeding as in example 2, but replacing the 4-fluorobenzoic acid by the appropriate acid, there were prepared:

i) (±)-trans-2-(2-furoyloxy)-N-methyl-1-(pyrid-3-yl)cyclohexanecarbothioamide, a white solid, m.p. 235°–237° C.;

ii) (±)-trans-N-methyl-1-(pyrid-3-yl)-2-(thien-2-oyloxy)cyclohexanecarbothioamide, a white solid, m.p. 228°–230° C.;

iii) cis/trans-[(2-N-methyl{thiocarbamoyl}-2-{pyrid-3-yl}cyclohexyloxycarbonyl)methyl]trimethylammonium chloride, a white crystalline solid, m.p. 210°–211° C.;

iv) (±)-trans-[3-(2-N-methyl{thiocarbamoyl}-2-{pyrid-3-yl}cyclohexyloxycarbonyl)propyl]trimethylammonium chloride pentahydrate, a cream solid, m.p. 100° C. (softens);

v) (±)-trans-N-methyl-2-[(2-methyl-5-nitroimidazol-1-yl)acetoxy]-1-(pyrid-3-yl)cyclohexanecarbothioamide, a white crystalline solid, m.p. 191°–192° C.;

vi) (±)-trans-N-methyl-2-(1-phenylcyclopropylcarbonyloxy)-1-(pyrid-3-yl)cyclohexanecarbothioamide, a white solid, m.p. 193°–195° C.;

vii) (±)-trans-2-diphenylacetoxy-N-methyl-1-(pyrid-3-yl)cyclohexanecarbothioamide, a white solid, m.p. 164°–166° C.;

viii) (±)-trans-N-methyl-2-(3-phenylpropenoyloxy)-1-(pyrid-3-yl)cyclohexanecarbothioamide, a white crystalline solid, m.p. 175°–176.5° C.;

ix) N,N-dimethylglycine (±)-trans-[N-methyl(thiocarbamoyl)]-2-(pyrid-3-yl)cyclohexyl ester, a white powder, m.p. 153°–155° C.;

x) (±)-trans-2-[2-(3-benzoylphenyl)propanoyloxy]-N-methyl-1-(pyrid-3-yl)cyclohexanecarbothioamide, a white solid, m.p. 158°–160° C.;

xi) (±)-trans-2-cyclopropanoyloxy-N-methyl-1-(pyrid-3-yl)cyclohexanecarbothioamide, a white solid, m.p. 171°–176° C.;

xii) (±)-trans-2-methoxyacetoxy-N-methyl-1-(pyrid-3-yl)cyclohexanecarbothioamide, a white crystalline solid, m.p. 145°–146° C.;

xiii) (±)-trans-N-methyl-2-phenoxyacetoxy-1-(pyrid-3-yl)cyclohexanecarbothioamide, a white crystalline solid, m.p. 170°–171° C.;

xiv) (±)-trans-2-cyanoacetoxy-N-methyl-1-(pyrid-3-yl)cyclohexanecarbothioamide, a fawn crystalline solid, m.p. 166°–167° C.

[Found: C, 60.4; H, 6.0; N, 13.3; S, 10.2%
Calculated for $C_{16}H_{19}N_3O_2S$: C, 60.5; H, 6.0; N, 13.2; S, 10.1%]; and xv) (±)-trans-N-methyl-2-(3-phenylpropanoyloxy)-1-(pyrid-3-yl)cyclohexanecarbothioamide, a white solid, m.p. 140°–142° C.

EXAMPLE 14

Compounds Y, AN and AS

By proceeding as in Example 1, but replacing the butyric anhydride with the appropriate anhydride, there were prepared:

i) (±)-trans-N-methyl-2-(pyrid-4-ylcarbonyloxy)-1-(pyrid-3-yl)cyclohexanecarbothioamide, a white solid, m.p. 208°–210° C.;

ii) (±)-trans-N-methyl-1-(pyrid-3-yl)-2-trimethylacetoxycyclohexanecarbothioamide, off white needles, m.p. 202°–203° C.; and iii) (±)-trans-2-(2-cyano-3-phenylpropenoyloxy)-N-methyl-1-(pyrid-3-yl)cyclohexanecarbothioamide, a cream crystalline solid, m.p. 179°–180° C. (dec).

EXAMPLE 15

Compounds AB, AC, AQ and AR

By proceeding as in Examples 7 (for the benzoates) or 1 (for the acetates), but replacing the pyrid-3-yl compound by the appropriate quinolin-3-yl compound, there were prepared:

(±)-cis-2-benzoyloxy-N-methyl-1-(quinolin-3-yl)cyclohexanecarbothioamide, a white powder, m.p. 256°–258° C.;

ii) (±)-trans-2-benzoyloxy-N-methyl-1-(quinolin-3-yl)cyclohexanecarbothioamide, a white powder, m.p. 231°–232° C.;

iii) (±)-cis-2-acetoxy-N-methyl-1-(quinolin-3-yl)cyclohexanecarbothioamide, a pale yellow powder, m.p. 190°–192° C.; and iv) (±)-trans-2-acetoxy-N-methyl-1-(quinolin-3-yl)cyclohexanecarbothioamide, a white powder, m.p. 212°–213° C.

EXAMPLE 16

Compound AH

A solution of (±)-trans-N-methyl-2-hydroxy-1-(pyrid-3-yl)cyclohexanecarbothioamide (1.5 g, 6 mmol) in a mixture of anhydrous pyridine (5 ml) and dichloromethane (15 ml) at 20° C. was treated with 4-dimethylaminopyridine (0.88 g, 7.2 mmol) followed by acetoxyacetyl chloride (1.02 g, 7.5 mmol) dropwise over 5 minutes. After 9 hours at 20° C. the mixture was concentrated in vacuo (20° C.; 0.1 mmHg) and the crude product was partitioned between dichloromethane (20 ml) and saturated aqueous sodium bicarbonate solution (20 ml). The organic phase was dried over magnesium sulphate and then concentrated in vacuo to give a crude oil (1.3 g) which was dissolved in a mixture of dichloromethane (10 ml) and acetone (10 ml) and then filtered through a pad of flash silica. The filtrate was concentrated in vacuo to give a crude solid which was recrystallized from toluene to give (±)-trans-2-acetoxyacetoxy-N-methyl-1-(pyrid-3-yl)cyclohexanecarbothioamide, as a white powder, (0.85 g, 2.4 mmol), m.p. 130°–132° C.;

[Found: C, 58.7; H, 6.4; N, 8.1; S, 9.3%

Calculated for $C_{17}H_{22}N_2O_4S$: C, 58.3; H, 6.3; N, 8.0; S, 9.15%]

EXAMPLE 17

Compound AO

A stirred solution of (±)-trans-N-methyl-1-(pyrid-3-yl)-2-succinyloxycyclohexanecarbothioamide (0.5 g, 1.4 mmol), methanol (0.45 g, 14 mmol) and 4-dimethylaminopyridine (350 mg, 2.8 mmol) in acetonitrile (5 ml) at 20° C. was treated with dicyclohexylcarbodiimide (0.59 g, 2.8 mmol). After 18 hours at 20° C. the mixture was filtered and the filtrate concentrated in vacuo. The residue was dissolved in dichloromethane (20 ml) and washed with hydrochloric acid (0.1M, 20 ml). The organic phase was then washed with sodium carbonate solution (2M) and dried over sodium sulphate. Concentration in vacuo afforded a crude oil which was recrystallized from a 9:1 mixture of diisopropyl ether and methanol to give (±)-trans-2-(3-methoxycarbonylpropanoyloxy)-N-methyl-1-(pyrid-3-yl)cyclohexanecarbothioamide, as a white solid, (100 mg, 0.27 mmol), m.p. 115°–117° C.;

[Found: C, 59.7; H, 7.0; N, 7.9%

Calculated for $C_{18}H_{24}N_2O_4S$ C, 59.3; H, 6.6; N, 7.7%].

EXAMPLE 18

Compounds AW, AX and BC i) 1,1-Carbonyldiimidazole (0.97 g, 6 mmol) was added to a stirred suspension of (±)-trans-N-methyl-1-(pyrid-3-yl)-2-succinyloxycyclohexanecarbothioamide (1.05 g, 3 mmol) in dichloromethane (50 ml) at 20° C. After 30 minutes at 20° C. the resulting clear solution was treated with a 33% solution of methylamine in ethanol (0.19 g, 6 mmol) and stirred for a further 18 hours at 20° C. The solution was then washed with water (2×25 ml) and dried over magnesium sulphate. Concentration in vacuo afforded a crude oil which was recrystallized from aqueous methanol to give (±)-trans-N-methyl-2-[3-(N-methylcarbamoyl)propanoyloxy]-1-(pyrid-3-yl)cyclohexanecarbothioamide, as a white solid, (0.58 g, 1.6 mmol), m.p. 190°–192° C.;

[Found: C, 59.0; H, 7.0; N, 11.2; S, 8.7%

Calculated for $C_{18}H_{25}N_3O_3S$: C, 59.5; H, 6.9; N, 11.6; S, 8.8%].

By proceeding in a similar manner, but replacing the methylamine by the appropriate amine, there were prepared:

ii) (±)-trans-N-methyl-2-[3-(4-methylpiperazin-1-ylcarbonyl)propanoyloxy]-1-(pyrid-3-yl)cyclohexanecarbothioamide monohydrate, a white solid on recrystallization from water, m.p. 100° C. (dec);

[Found: C, 58.2; H, 7.6; N, 12.2; S, 7.2%

Calculated for $C_{22}H_{32}N_4O_3S \cdot H_2O$: C, 58.6; H, 7.6; N, 12.4; S, 7.1%]; and iii) (±)-trans-2-[3-(N,N-dimethylcarbamoyl)propanoyloxy]-N-methyl-1-(pyrid-3-yl)cyclohexanecarbothioamide, a white solid on recrystallization from ethyl acetate, m.p. 155°–157° C.;

[Found: C, 60.5; H, 7.4; N, 11.1; S, 8.4%

Calculated for $C_{19}H_{27}N_3O_3S$: C, 60.5; H, 7.2; N, 11.1; S, 8.5%].

EXAMPLE 19

Compound AY

To a stirred solution of (±)-trans-2-hydroxy-N-methyl-1-(pyrid-3-yl)cyclohexanecarbothioamide (3.26 g, 13.00 mmol) in a warm mixture of dichloromethane/pyridine (3:1, 65 ml) were added sequentially sodium tetrahydropyran-2-yloxyacetate (3.64 g, 20.00 mmol), dicyclohexylcarbodiimide (5.37 g, 26.02 mmol) and 4-dimethylaminopyridine (0.10 g). The resulting mixture was treated at 25° C. with pyridine hydrochloride (2.31 g., 20.00 mmol) during 1–2 minutes, following which an exothermic reaction set in, raising temperature to 40° C. and accompanied by the precipitation of a solid. The suspension was stirred for a further 30 minutes as temperature fell to 25° C. and for 1.5 hours thereafter.

The mixture was diluted with water (260 ml) and extracted dichloromethane (260+2×65 ml), the insoluble material being removed by filtration during the first extraction. The combined extracts were washed successively with saturated aqueous sodium hydrogen carbonate solution (130 ml) and saturated brine solution (130 ml), dried and the solvent evaporated in vacuo to give a syrup, which crystallized upon trituration with diethyl ether at 0° C. The solid was recrystallized from a mixture of dichloromethane/petroleum ether (b.p. 60°–80° C.) to afford (±)-trans-N-methyl-1-(pyrid-3-yl)-2-(tetrahydropyran-2-yloxy)acetoxycyclohexanecarbothioamide, (4.45 g, 10.52 mmol), as a colorless solid, m.p. 132.5°–134° C.;

[Found: C, 61.3; H, 7.4; N, 7.2; S, 7.9%

Calculated for $C_{20}H_{28}N_2O_4S$: C, 61.2; H, 7.2; N, 7.1; S, 8.2%].

EXAMPLE 20

Compound AZ

A stirred solution of (±)-trans-N-methyl-2-hydroxy-1-(pyrid-3-yl)cyclohexanecarbothioamide (1.25 g, 5 mmol) in a mixture of acetonitrile (50 ml) and dimethylformamide (5 ml) at 20° C. was treated with 4-dimethylaminopyridine (0.12 g) followed by N-t-butoxycarbonylphenylalanine (1.39 g, 5.3 mmol) and dicyclohexylcarbodiimide (1.65 g, 8 mmol). The reaction mixture was then stirred at 20° C. for 18 hours. After filtration the solution was concentrated in vacuo (40° C.; 0.1 mmHg). The residue was dissolved in dichloromethane (60 ml) and washed successively with hydrochloric acid (0.2M, 50 ml), sodium carbonate solution (2M, 10 ml) and brine (10 ml). After drying over sodium sulphate the solvent was removed in vacuo to give (±)-trans-2-(t-butoxycarbonylamino)-3-phenylpropanoyl-N-methyl-1-(pyrid-3-yl)cyclohexanecarbothioamide (2.37 g), m.p. 55°–60° C., which was used in the next step without further purification.

(±)-trans-2-(t-Butoxycarbonylamino)-3-phenylpropanoyl-N-methyl-1-(pyrid-3-yl)cyclohexanecarbothioamide (2.4 g) was added to trifluoroacetic acid (20 ml) at 0° C. After 1 hour the solution was concentrated in vacuo and the residue washed with diethyl ether (20 ml). The residue was then disolved in dichlomethane (30 ml), washed with sodium bicarbonate solution (10%, 20 ml) and dried over magnesium sulphate. After filtration and concentration in vacuo the residue was recrystallized from diisopropyl ether/ethyl acetate to give L-phenylalanine (±)-trans-[N-methyl(thiocarbamoyl)]-2-(pyrid-3-yl)cyclohexyl ester (0.9 g), as a white powder, m.p. 140°–141° C.

[Found: C, 66.5; H, 6.9; N, 10.5; S, 7.6%

Calculated for $C_{22}H_{27}N_3O_2S$: C, 66.4; H, 6.8; N, 10.6; S, 8.0%].

EXAMPLE 21

Compounds BE and BA i) A solution of (±)-trans-N-methyl-2-hydroxy-1-(pyrid-3-yl)cyclohexanecarbothioamide (1.25 g, 5 mmol), N-t-butoxycarbonylglycine (0.92 g, 5.25 mmol) and 4-dimethylaminopyridine (0.25 g) in a mixture of acetonitrile (50 ml) and dimethylformamide (5 ml) at 20° C. was treated with dicyclohexylcarbodiimide (1.65 g, 8 mmol) and stirred at 20° C. for 18 hours. After filtration the solution was concentrated in vacuo (40° C.; 0.1 mmHg). The residue was dissolved in dichloromethane (60 ml) and washed successively with hydrochloric acid (0.2M, 50 ml), sodium carbonate solution (2M, 10 ml) and brine (10 ml). After drying over sodium sulphate the solvent was removed in vacuo to give (±)-trans-2-t-butoxycarbonylaminoacetoxy-N-methyl-1-(pyrid-3-yl)cyclohexanecarbothioamide, as a white solid (1.2 g) m.p. 159°–161° C.;

[Found: C, 59.4; H, 7.4; N, 10.5%

Calculated for $C_{20}H_{29}N_3O_4S$: C, 59.0; H, 7.2; N, 10.3%].

ii) (±)-trans-2-t-Butoxycarbonylaminoacetoxy-N-methyl-1-(pyrid-3-yl)cyclohexanecarbothioamide (1.2 g) was added to trifluoroacetic acid (20 ml) at 0° C. After 1 hour the solution was concentrated in vacuo and the residue washed with diethyl ether (20 ml). The residue was then dissolved in dichloromethane (20 ml) and washed with sodium bicarbonate solution (10%, 20 ml). After drying over magnesium sulphate the solvent was removed in vacuo to give a crude oil which was recrystallized from ethyl acetate to give glycine (±)-trans-[N-methyl(thiocarbamoyl)]-2-(pyrid-3-yl)cyclohexyl ester, as a white solid, (0.4 g) m.p. 180°–181° C.;

[Found: C, 58.4; H, 7.0; N, 13.7; S, 10.4%

Calculated for: $C_{15}H_{21}N_3O_2S$ C, 58.6; H, 6.9; N, 13.7; S, 10.4%].

EXAMPLE 22

Compound BB

A solution of (±)-trans-N-methyl-1-(pyrid-3-yl)-2-(tetrahydropyran-2-yloxy)acetoxycyclohexane carbothioamide (2.40 g, 6.11 mmol) in a mixture of acetic acid (7.2 ml), tetrahydrofuran (4.8 ml) and water (12.0 ml) was stirred and heated at 50°–55° C. for 10 hours in an open flask, diluted with water (100 ml) and extracted using dichloromethane (100+3×50 ml). The combined extracts were washed with saturated aqueous sodium hydrogen carbonate solution (100 ml) and dried over anhydrous magnesium sulphate. The latter was removed by filtration, extracted with a warm mixture of dichloromethane/acetone (4:1, 100 ml) and the filtered extract combined with the dichloromethane extracts. The solvents were removed in vacuo to give a waxy solid, which was recrystallized from a mixture of dichloromethane/acetone (1:1) by evaporation of the dichloromethane to afford (±)-trans-2-hydroxyacetoxy-N-methyl-1-(pyrid-3-yl)cyclohexanecarbothioamide (1.58 g, 5.12 mmol), as a colorless solid, m.p. 200°–200.5° C.

Found: C, 58.8; H, 6.8; N, 9.1; S, 10.2%

Calculated for $C_{15}H_{20}N_2O_3S$: C, 58.4; H, 6.5; N, 9.1; S, 10.4%].

REFERENCE EXAMPLE 1

A stirred solution of(±)-N-methyl-2-oxo-1-(pyrid-3-yl)cyclohexanecarbothioamide (1.7 g, 6.9 mmol) in methanol (4 ml) at 0° C. was treated with sodium borohydride (262 mg, 6.9 mmol). After 10 minutes at 0° C. the mixture was warmed to 20° C. and a solution formed. It was then cooled to 0° C. and stirred for a further 40 minutes. The reaction mixture was then treated with brine (10 ml) and water (30 ml) and extracted with ethyl acetate (2×50 ml). The combined organic extracts were washed with brine (10 ml) then dried over anhydrous sodium sulphate. After concentration in vacuo (30° C.; 14 mmHg) the product was fractionally recrystallized from cyclohexane/ethyl acetate (6:1) (10 ml) to afford:

i) (±)-trans-N-methyl-2-hydroxy-1-(pyrid-3-yl)cyclohexanecarbothioamide (1.4 g, 5.6 mmol), m.p. 171°–172° C.;

[N.M.R. (CDCl$_3$): 1.24–2.02 (m, 6H); 2.08–2.28 (dt, 1H), 2.46–2.60 (m, 1H), 3.06–3.12 (d, 3H), 3.54–3.78 (br s, 1H), 4.70–4.86 (m, 1H), 7.26–7.28 (m, 1H), 7.44–7.70 (br, s, 1H), 8.20–8.28 (dt, 1H), 8.48–8.58 (dd, 1H), 8.92–8–96 (d, 1H)

Found: C, 62.3; H, 7.3; N, 11.4; 12.7%

Calculated for $C_{13}H_{18}N_2OS$: C, 62.4; H, 7.3; N, 11.2; S, 12.8%]; and ii) (±)-cis-N-methyl-2-hydroxy-1-(pyrid-3-yl)cyclohexanecarbothioamide (0.2 g 0.8 mmol), m.p. 169°-172° C.;

[N.M.R (CDCl₃): 1.32-2.06 (c, 7H), 2.88-3.04 (m, 1H), 3.22-3.30 (d, 3H}, 4.36-4.48 (dd, 1H), 5.46-6.06 (br s, 1H), 7.14-7.26 (m, 1H), 7.81-7.92 (m, 1H), 8.16-8.24 (dd, 1H), 8.52-8.60 (m, 1H)

Found: C, 62.0; H, 7.3; N, 11.1; S, 12.7%

Calculated for $C_{13}H_{18}N_2OS$; C, 62.4; H, 7.3; N, 11.2; S, 12.8%]

REFERENCE EXAMPLE 2

A vigorously stirred solution of (±)-2-(pyrid-3-yl)cyclohexanone (5.5 g, 30 mmol) in anhydrous tetrahydrofuran (50 ml) under argon at −15° C. was treated with potassium t-butoxide (3.36 g, 30 mmol).

After 60 minutes at 0° C., a solution of methyl isothiocyanate (2.4 g, 33 mmol) in anhydrous tetrahydrofuran (10 ml) was added during 5 minutes. After 2.5 hours at 0° C. the solution was warmed to 20° C. and then poured into a saturated aqueous brine solution (250 ml). The mixture was extracted with ethyl acetate (50 ml) and then with chloroform (3×50 ml). The combined organic extracts were dried over sodium sulphate and then concentrated in vacuo (30° C.; 14 mmHg).

The crude product was recrystallized from methanol to give (±)-N-methyl-2-oxo-1-(pyrid-3-yl)cyclohexanecarbothioamide (4.8 g, 19 mmol), m.p. 188°-190° C.;

[N.M.R. (CDCl₃): 1.62-2.06 (m, 4H), 2.42-2.60 (m, 2H), 2.60-2.82 (m, 1H), 2.84-3.06 (m, 1H), 3.16-3.2 (d, 3H), 7.24-7.34 (ddd, 1H), 7.6-7.68 (ddd, 1H), 8.43-8.47 (d, 1H), 8.48-8.54 (dd, 1H), 8.9-9.2 (br s, 1H)

Found: C, 62.9; H, 6.6; N, 11.3; S, 13.1%

Calculated for $C_{13}H_{16}N_2OS$: C, 62.9; H, 6.5; N, 11.3; S, 12.9%].

REFERENCE EXAMPLE 3

A solution of (±)-trans-1-[(pyrid-3-yl)bromomethyl]-cyclopentanol (10.24 g, 40 mmol) in anhydrous tetrahydrofuran (500 ml) at 0° C. was treated, dropwise during 30 minutes, with a solution of silver perchlorate (9.9 g, 48 mmol) in anhydrous tetrahydrofuran (50 ml). After 60 minutes at 0° C. the mixture was poured into a mixture of saturated aqueous brine solution (500 ml) and 10% w/v aqueous sodium bicarbonate solution (500 ml). The resulting mixture was filtered and then extracted with ethyl acetate (2×500 ml). The combined organic extracts were washed with brine and then dried over sodium sulphate. Concentration in vacuo (30° C.; 14 mmHg) afforded a crude oil which was recrystallized from cyclohexane (120 ml) to give (±)-2-(pyrid-3-yl)-cyclohexanone (6.7 g, 38 mmol), m.p. 78°-80° C.;

[N.M.R. (CDCl₃): 1.72-2.12 (m, 4H), 2.12-2.40 (m, 2H), 2.40-2.64 (m, 2H), 3.56-3.72 (dd, 1H), 7.22-7.32 (m, 1H), 7.44-7.54 (ddd, 1H), 8.34-8.42 (dd, 1H), 8.46-8.54 (dd, 1H)].

REFERENCE EXAMPLE 4

A solution of 3-cyclopentylidenemethylpyridine (62.2 g, 0.39 mol) in acetone (600 ml) and water (100 ml) was treated with a solution of concentrated sulphuric acid (18.9 g, 0.19 mol) in water (100 ml) at 5° C. The ice-cold solution was treated with 1,3-dibromo-5,5-dimethylhydantoin (55 g, 0.19 mol) during 20 minutes. After 3.5 hours at 0° C. the mixture was treated with sodium bicarbonate (33.6 g, 0.4 mol) followed by water (2 l) and then extracted with ethyl acetate (2×500 ml). The organic phase was removed and washed with 10% w/v aqueous sodium bicarbonate solution (500 ml) followed by water (200 ml) and brine (200 ml). The crude extract was dried over sodium sulphate and then filtered through a column of flash silica gel (10 cm×2.4 cm diameter). After concentration in vacuo (20° C.; 14 mmHg) the dark oil crystallized on standing to give (±)-trans-1-[(pyrid-3-yl)bromomethyl]cyclopentanol (56 g, 0.22 mol) m.p. 92°-94° C.; [N.M.R. (CDCl₃) 1.36-2.06 (c, 8H), 2.32-2.46(br s, 1H), 5.02 (s, 1H), 7.24-7.34 (ddd, 1H), 8.0-8.1 (ddd, 1H), 8.52-8.56 (dd, 1H), 8.62-8.66 (d, 1H)

Found: C, 51.9; H, 5.6; Br, 30.6; N, 5.5%

Calculated for $C_{11}H_{14}BrNO$: C, 51.6; H, 5.5; Br, 31.2; N, 5.5%].

REFERENCE EXAMPLE 5

A suspension of cyclopentyltriphenylphosphonium bromide (226 g, 0.55 mol) in anhydrous tetrahydrofuran (1000 ml) at 2° C. was treated with vigorous stirring under an atmosphere of argon, with potassium t-butoxide (61.7 g, 0.55 mol). The dark red mixture was stirred at 5° C. for 80 minutes and then treated with pyridine-3-carbaldehyde (58.9 g, 0.55 mol) during a period of 20 minutes. The reaction mixture was stirred at 0° C. for 2 hours and then at 20° C. for 18 hours. The tetrahydrofuran was removed in vacuo (30° C.; 14 mmHg) and the residue extracted with pentane (2×500 ml) After treatment with decolourising charcoal (5 g), the mixture was filtered through a plug of flash silica gel (Merck 70-230 mesh; 13 cm×2 cm diameter). The filtrate was concentrated in vacuo (30° C., 14 mmHg; then 20° C., 0.01 mmHg) to afford 3-cyclopentylidenemethylpyridine (54 g, 0.34 mol) as an orange oil which was used without further purification;

[N.M.R (CDCl₃): 1.6-1.95 (m, 4H), 2.4-2.65 (m, 4H), 6.26-6.34 (m, 1H), 7.16-7.25 (ddd, 1H), 7.56-7.65 (ddd, 1H), 8.52-8.52 (d, 1H)].

REFERENCE EXAMPLE 6A

A 4:1 mixture of (±)-cis/trans-2-methoxy-1-(pyrid-3-yl)cyclohexanol (2 g, 10 mmol), toluene and phosphorus pentoxide (3.4 g, 24 mmol) was heated at reflux for 5 hours. The mixture was then filtered and the precipitate partitioned between sodium hydroxide solution (2M, 80 ml) and diethyl ether (25 ml). The aqueous layer was extracted with ether (3×25 ml) and the combined organic extracts were dried over sodium sulphate. Concentration in vacuo afforded a crude oil which was purified by flash chromatography to give 2-(pyrid-3-yl)cyclohexanone (0.7 g, 4 mmol).

REFERENCE EXAMPLE 6B (±)-cis/trans-2-Methoxy-1-(pyrid-3-yl)cyclohexanol (270.6 g) was added dropwise to concentrated sulphuric acid (1.6l). The temperature rose to 40° C. and cold water cooling was used to prevent this being exceeded. The dark red/brown solution was stirred for 6.5 hours as its temperature fell to 28° C.

The solution was added to vigorously stirred ice/water (15l) and the brown mixture stirred for 10 minutes until its temperature had dropped to −5° C. Aqueous sodium hydroxide (12M, 4.82l) was added over 30 minutes until the pH reached 5. A further 10l of ice was added during this addition to prevent the temperature rising above 30° C. Sodium carbonate (88 g) was then added portionwise to pH8, followed by sodium chloride (5.3 kg).

Diethyl ether (5l) was added and the mixture stirred vigorously. The ether was separated and the aqueous layer extracted with further quantities of diethyl ether (5l+4l+3l+2l). The combined extracts were dried (MgSO$_4$) and evaporated to give a yellow solid. This was triturated with diethyl ether (500 ml) to give 2-(pyrid-3-yl)cyclohexanone (200 g) as a cream solid.

REFERENCE EXAMPLE 7

To a solution of 2.5M n-butyllithium in hexane (13.2 ml, 33 mmol) at −78° C. was added diethyl ether (15 ml) followed by a solution of 3-bromopyridine (4.7 g, 30 mmol) in ether (90 ml) over a period of 10 minutes. After 1 hour at −78° C. a solution of (±)-2-methoxycyclohexanone (3.84 g, 30 mmol) in ether (20 ml) was added dropwise during 10 minutes. After 2 hours at −78° C. and 30 minutes at 0° C. the reaction mixture was warmed to 20° C. and then poured onto ice (150 g). The mixture was extracted with ether (2×50 ml) and then the combined organic extracts were extracted with 1N hydrochloric acid (50 ml). This aqueous extract was washed with ether (20 ml) and then treated with 2M sodium hydroxide solution (25 ml) and extracted with ether (3×100 ml). The organic extracts were combined, washed with brine then dried over anhydrous sodium sulphate. Concentration in vacuo afforded (±)-2-methoxy-1-(pyrid-3-yl)cyclohexanol (5.0 g, 24 mmol) as a 4:1 mixture of cis and trans isomers;

[N.M.R. (CDCl$_3$): 1.2–2.14 (c), 2.24–2.44 (m), 2.90–3.28 (c), 3.48–3.60 (m), 7.18–7.30 (m), 7.78–7.96 (m), 8.40–8.48 (m), 8.62–8.72 (m), 8.78–8.82 (m)].

REFERENCE EXAMPLE 8

A stirred solution of (±)-N-methyl-2-oxo-1-(quinolin-3-yl)cyclohexanecarbothioamide (5 g, 16.8 mmol) in a mixture of dichloromethane (120 ml) and ethanol (60 ml) at −70° C. was treated with sodium borohydride (0.7 g, 18.5 mmol) over 10 minutes. After 4 hours at −70° C. the mixture was allowed to warm to −40° C. over 1 hour, and then treated with a mixture of glacial acetic acid (10 ml) and water (200 ml). After 10 minutes at 20° C. the aquous layer was removed and extracted with dichloromethane (2×50 ml). The combined organic fractions were washed with saturated sodium bicarbonate solution (2×30 ml) and brine (20 ml) and dried over magnesium sulphate. Concentration in vacuo (40° C.; 25 mmHg) to give a crude oil (6.5 g) which was purified by flash column chromatrography eluting with ethyl acetate to give (±)-trans-N-methyl-2-hydroxy-1-(quinolin-3-yl)cyclohexanecarbothioamide (1.3 g, 3.3 mmol), m.p. 191°–193° C.;

[Found: C, 67.6; H, 6.7; N, 9.5; S, 10.6%
Calculated for C$_{17}$H$_{20}$N$_2$OS: C, 68.0; H, 6.7; N, 9.3; 10.7%].

The reaction also produced (±)-cis-N-methyl-2-hydroxy-1-(quinolin-3-yl)cyclohexanecarbothioamide, which could be isolated from the mother liquors, m.p. 243°–245° C.;

[Found: C, 68.4; H, 6.8; N, 9.4; S, 10.6%
Calculated for C$_{17}$H$_{20}$N$_2$OS: C, 68.0; H, 6.7; N, 9.3; 10.7%].

REFERENCE EXAMPLE 9

A solution of (±)-2-(quinolin-3-yl)cyclohexanone (0.78 g, 3.5 mmol) in tetrahydrofuran (10 ml) at −5° C. was treated with potassium t-butoxide (0.43 g, 3.9 mmol) in one portion. After 25 minutes at −5° C. the deep red mixture was treated dropwise during 1 minute with a solution of methyl isothiocyanate (0.28 g, 3.9 mmol) in tetrahydrofuran (2 ml). After 4 hours at 0° C. the reaction mixture was partitioned between saturated aqueous ammonium chloride solution (50 ml) and chloroform (50 ml). The aqueous layer was extracted again with chloroform (50 ml). The combined organic extracts were then dried over sodium sulphate and concentrated in vacuo (20° C.; 14 mmHg) to give a crude oil which was purified by flash chromatography over silica gel eluting with ethyl acetate to give (±)-N-methyl-2-oxo-1-(quinolin-3-yl)cyclohexanecarbothioamide (0.1 g, 0.33 mmol), m.p. 235°–236° C.;

[N.M.R. (CDCl$_3$): 1.7–2.18 (c, 4H), 2.46–2.64 (m, 2H), 2.72–2.90 (m, 1H), 2.96–3.16 (m, 1H), 3.16–3.22 (d, 3H), 7.50–7.62 (ddd, 1H), 7.66–7.76 (ddd, 1H), 7.76–8.02 (dd, 1H), 8.0 (d, 1H), 8.04–8.12 (dd, 1H), 8.78–8.80 (d, 1H), 8.92–9.18 (br s, 1H)

Found: C, 68.0; H, 5.8; N, 9.0; S, 10.4%
Calculated for C$_{17}$H$_{18}$N$_2$OS: C, 68.4; H, 6.08; N, 9.4; S, 10.7%].

REFERENCE EXAMPLE 10

A solution of (±)-trans-1-[(quinolin-3-yl)bromomethyl)cyclopentanol (1.1 g, 3.6 mmol) in tetrahydrofuran (20 ml) at 0° C. was treated, dropwise during 2 minutes, with a solution of silver perchlorate (893 mg, 4.3 mmol) in tetrahydrofuran (5 ml). After 1 hour at 0° C. a mixture of saturated brine solution (20 ml) and saturated aqueous sodium bicarbonate solution (20 ml) was added to the reaction mixture. Ethyl acetate (40 ml) was then added and the resulting mixture was filtered through diatomaceous earth. The aqueous layer was removed and extracted with ethyl acetate (50 ml). The combined organic extracts were washed with brine (30 ml), dried over sodium sulphate then concentrated invacuo to afford (±)-2-(quinolin-3-yl)cyclohexanone (0.8 g, 3.5 mmol) as an oil which solidified on standing m.p. 114°–115° C.;

[N.M.R.(CDCl$_3$) 1.72–2.68 (c, 8H), 3.74–3.88 (dd, 1H), 7.46–7.56 (ddd, 1H), 7.62–7.70 (ddd, 1H), 7.72–7.82 (dd, 1H), 7.88–7.96 (d, 1H), 8.04–8.12 (d, 1H), 8.68 (d, 1H)].

REFERENCE EXAMPLE 11

A mixture of 3-cyclopentylidenemethylquinoline (3 g, 14 mmol), water (100 ml), dimethyl sulphoxide (50 ml), acetone (100 ml) and concentrated sulphuric acid (3.4 ml, 35 mmol) at 5° C. was treated with 1,3-dibromo-5,5-dimethylhydantoin (4.0 g, 14 mmol). After 5 minutes at 5° C. the mixture was stirred for 2 hours at 20° C. The mixture was filtered and washed with ethyl acetate (2×50 ml). The aqueous phase was then treated with saturated aqueous sodium bicarbonate solution (50 ml) and extracted with ethyl acetate (100 ml). The organic phase was then washed with water (50 ml) and brine (50 ml) and dried over sodium sulphate. Concentration in vacuo afforded a crude oil which was purified by flash chromatography eluting with a mixture of diethyl ether and hexane (50:50) and then ether. The product so obtained was then recrystallized from cyclohexane to give (±)-trans-1-[(quinolin-3-yl)-bromomethyl]cyclopentanol (1.1 g, 3.6 mmol);

[N.M.R.: 1.44–1.85 (c, 4H), 1.8–2.06 (c, 4H), 5.06 (s, 1H), 7.44–7.56 (ddd, 1H), 7.60–7.72 (ddd, 1H), 1H), 9.0 (d, 1H)].

REFERENCE EXAMPLE 12

A solution of 2-chloro-3-cyclopentylidenemethylquinoline (7.6 g, 31.3 mmol) in glacial acetic acid (80 ml) at 60° C. was treated with zinc powder (4.0 g, 62.6 mmol). After stirring at 60° C. for 3 hours, the reaction mixture was cooled and then treated dropwise with aqueous sodium hydroxide solution (2M, 330 ml); the temperature being kept below 20° C. throughout. The resulting mixture was then extracted with ethyl acetate (2×250 ml). The combined organic extracts were dried over sodium sulphate then concentrated in vacuo (30° C., 14 mmHg) to give a crude red oil (8 g) which was extracted with hot pentane (2×200 ml). Concentration of the combined extracts in vacuo (20° C.; 14 mmHg) afforded 3-cyclopentylidenemethylquinoline (4 g, 31 mmol) which was used without further purification;

[N.M.R. (CDCl$_3$): 1.6–1.96 (m, 4H), 2.5–2.72 (m, 4H), 6.50 (m, 1H), 7.46–7.58 (ddd, 1H), 7.60–7.68 (ddd,1H), 7.76–7.80 (dd, 1H), 8.0–8.08 (c, 2H)].

REFERENCE EXAMPLE 13

A suspension of cyclopentyltriphenylphosphonium bromide (4.1 g, 10 mmol) in tetrahydrofuran (50 ml) at 0° C. was treated with potassium t-butoxide (1.1 g, 10 mmol) portionwise during 5 minutes. After 1 hour at 0° C. the deep red mixture was treated with 2-chloroquinoline-3-carbaldehyde (1.9 g, 10 mmol). After 4 hours at 0° C. hexane (250 ml) followed by brine (50 ml) was added to the reaction mixture. The organic layer was removed and dried over sodium sulphate. After concentration in vacuo (30° C.; 14 mmHg) the crude oil was recrystallized from hexane to give 2-chloro-3-cyclopentylidenemethyl. quinoline (1.7 g, 7 mmol); m.p. 84°–86° C.;

[N.M.R. (CDCl$_3$): 1.64–1.90 (m, 4H), 2.44–2.66 (m, 4H), 6.52 (m,1H), 7.44–7.56 (ddd, 1H), 7.58–7.68 (ddd, 1H), 7.70–7.78 (dd, 1H), 7.92–8.00 (dd, 1H), 8.04 (s, 1H)

Found: C, 74.3; H, 5.8; Cl, 14.6, N, 5.7%

Calculated for $C_{15}H_{14}ClN$: C, 73.9; H, 5.8; Cl, 14.5; N, 5.7%].

REFERENCE EXAMPLE 14

A mixture of 3:1 cis/trans-(±)-2-methoxy-1-(quinolin-3-yl)cyclohexanol (1.35 g, 5.3 mmol) and 40% w/v sulphuric acid (25 ml) was refluxed for 1 hour. The cooled mixture was basified with sodium carbonate solution (1M, 200 ml) and the mixture extracted with ethyl acetate (3×125 ml). The combined organic extracts were washed with brine (30 ml) and dried over sodium sulphate. Concentration in vacuo afforded a crude oil (1.4 g) which was recrystallized from a 4:1 mixture of hexane and ethyl acetate (20 ml) to give (±)-2-(quinolin-3-yl)cyclohexanone (0.53 g, 2.3 mmol), m.p.114°–115° C.

REFERENCE EXAMPLE 15

A solution of 2.5M n-butyllithium in hexane (18 ml) in ether (30 ml) at −78° C. was treated dropwise with a solution of 3-bromoquinoline (4.7 g, 22.5 mmol) in ether (30 ml). After 1 hour at −78° C. a solution of (±)-2-methoxycyclohexanone (5.8 g, 45 mmol) in ether (30 ml) was added dropwise during 35 min to the reaction mixture, which was maintained at −78° C. for 2 hours then at 0° C. for 1 hour and then warmed to 20° C. during 1 hour. The reaction mixture was poured onto ice (50 g) and water (50 ml) and the resulting aqueous layer extracted with ether (3×50 ml). The combined organic extacts were treated with hydrochloric acid (2M, 75 ml) and the organic phase discarded. The aqueous layer was washed with ether (2×30 ml) and then basified with aqueous sodium hydroxide (2M, 75 ml). The aqueous layer was then extracted with ether (4×50 ml). The combined organic extracts were washed with brine (30 ml), dried over sodium sulphate and then concentrated in vacuo to afford a crude oil which was recrystallized from a 4:1 mixture of hexane and ethyl acetate (60 ml) to give a 3:1 mixture of (±)-cis/trans-2-methoxy-1-(quinolin-3-yl)cyclohexanol (3.2 g, 12 mmol), m.p. 114°–115° C.;

[N.M.R. (CDCl$_3$): essential features 3.06 (s, trans-OMe), 3.12 (cis- OMe).]

REFERENCE EXAMPLE 16 i) To a stirred suspension of [S]-(−)-N-methyl-2-oxo-1-(pyrid-3-yl)-cyclohexanecarbothioamide (1.0 g, 4 mmol) in dry isopropanol (50 ml) at 20° C. was added aluminium isopropoxide (0.99 g, 4.4 mmol). The mixture was then heated at reflux using a McIntyre head for slow solvent removal. After 2 hours the reaction mixture was replenished by the addition of more isopropanol (20 ml) and the mixture was refluxed for a further 2.5 hours. The mixture was then cooled to 20° C. After concentration in vacuo (40° C.; 14 mmHg), the residue was extracted with chloroform (2×20 ml) then washed with an aqueous solution of potassium sodium tartrate. The aqueous phase was extracted with chloroform (10 ml) and the combined organic phase were combined then washed with saturated sodium chloride and dried over magnesium sulphate. After filtration and concentration in vacuo the residue was recrystallized from acetonitrile to give [1S,2R]-trans-2-hydroxy-N-methyl-1-(pyrid-3-yl)cyclohexanecarbothioamide (0.79 g, 3.2 mmol), m.p. 158°–160° C.;

[N.M.R. (CD$_3$SOCD$_3$) 1.14–1.7 (c, 5H), 1.84–2.06, (m, 1H), 2.06–2.28 (m, 1H), 2.54–2.72 (m,1H), 2.94 (s, 3H), 4.46–5.1 (br s plus m, 2H), 7.22–7.36 (dd,1H), 7.81–7.95 (ddd,1H), 8.34–9.02 (dd,1H), 8.66–8.78 (dd,1H), 9.2–9.8 (br s)

Found: C, 62.1; H, 7.2; N, 11.1; S, 12.9%

Calculated for $C_{13}H_{18}N_2OS$: C, 62.4; H, 7.3; N, 11.2; S, 12.8% $[\alpha]_D^{25} = -146°$ (c=1.0, CHCl$_3$)].

ii) By proceeding in a similar manner, but replacing the [S] compound by the corresponding [R] compound, there was prepared [1R,2S]-trans-2-hydroxy-N-methyl-1-(pyrid-3-yl)cyclohexanecarbothioamide, m.p. 153°–155° C.;

[Found: C, 62.2; H, 7.2; N,11.1%

Calculated for $C_{13}H_{18}N_2OS$: C, 62.4; H, 7.3; N, 11.2%].

REFERENCE EXAMPLE 17

A solution of [2S]-anti-2-methoxymethyl-1-[2-(pyrid-3-yl)-2-methyl(thiocarbamoyl)cyclohexylideneamino]-pyrrolidine in aqueous hydrochloric acid (2M, 400 ml) was stirred at 60° C. for 12 hours. The solution was washed with methylene chloride (3×150 ml). The aqueous phase was brought to pH 8 with 2M aqueous sodium hydroxide solution. The precipitate was extracted into methylene chloride (500 ml +3×150 ml). The combined extracts were washed with water (3×50 ml) dried over magnesium sulphate and evaporated. The residual solid was washed with ethyl acetate (50 ml) and recrystallized from methanol to give the [S]-isomer of N-methyl-2-oxo-1-(pyrid-3-yl)cyclohexanecarbothioamide, colorless crystals (12.04 g), m.p. 193°–194° C., [α]$^{30}$ = −83° (CHCl$_3$).

REFERENCE EXAMPLE 18

A 2.5M solution of n-butyllithium in hexane (47 ml) was added dropwise to a stirred solution of [2S]-2-methoxymethyl-1-[2-(pyrid-3-yl)cyclohexylideneamino]pyrrolidine (50:50 mixture of diastereoisomers) (30.73 g) in dry tetrahydrofuran (410 ml) at −75° C. under argon during 15 minutes, to give a dark red solution. After 30 minutes, a solution of methyl isothiocyanate (8.63 g) in tetrahydrofuran (65 ml) was added during 10 minutes. The solution was allowed to warm to 0° C. during 45 minutes, maintained at this temperature for 1 hour and then at 20° C. for 1 hour, giving a yellow solution. This solution was quenched with saturated aqueous ammonium chloride solution (270 ml). The organic layer was separated and the aqueous layer extracted with ether (3×50 ml). The combined extracts were washed with brine (2×25 ml), dried over magnesium sulphate and evaporated (40° C.; 0.2 mmHg) to give crude [2S]-anti-2-(methoxymethyl)-1-[2-(pyrid-3-yl)-2-methyl(thiocarbamoyl)cyclohexylideneamino]pyrrolidine, a semi-crystalline oil (39.81 g).

REFERENCE EXAMPLE 19

A mixture of 2-(pyrid-3-yl)cyclohexanone (20.6 g, 117.6 mmol), [S]-(−)-1-amino-2-(methoxymethyl)pyrrolidine ('SAMP') (15.4 g, 118 mmol) and p-toluenesulphonic acid (316 mg) was refluxed in toluene (475 ml) for 4 hours. The toluene was removed in vacuo to afford an oil which was dissolved in diethyl ether (340ml) and washed with aqueous saturated sodium bicarbonate solution (2×170 ml). The organic phase was dried over magnesium sulphate then filtered and concentrated in vacuo to afford [2S]-2-(methoxymethyl)-1-[2-(pyrid-3-yl)cyclohexylidenamino]pyrrolidine (30.8 g, 113 mmol) as a 50:50 mixture of diastereoisomers;

[Found: C, 70.6; H, 8.5; N, 14.2%
Calculated for C$_{17}$H$_{25}$N$_3$O: C, 71.0;H, 8.8; N, 14.6%].

REFERENCE EXAMPLE 20

A solution of [2R]-anti-2-methoxymethyl-1-[2-(3-pyridyl)-2-methyl(thiocarbamoyl)cyclohexylideneamino]pyrrolidine (3.57 g, 9.9 mmol) in aqueous hydrochloric acid (2M, 36 ml) was stirred at 60° C. for 12 hours. The solution was washed with methylene chloride (3×15 ml). The aqueous phase was brought to pH 8 with aqueous sodium hydroxide solution. The precipitate was extracted into methylene chloride (3×15 ml). The combined extracts were washed with water (3×15 ml), dried over magnesium sulphate and evaporated. The residual solid was washed with ethyl acetate (5 ml) and recrystallized from methanol to give the [R]-isomer of N-methyl-2-oxo-1-(pyrid-3-yl)cyclohexanecarbothioamide, colorless crystals (0.95 g), m.p.185° C.;

[Found: C, 62.6; H,6.4; N, 11.3; S, 13.0%
Calculated for: C$_{13}$H$_{16}$N$_2$OS C, 62.9; H, 6.5; N, 11.3; S, 12.9%
[α]$^{30}$ = +90° (CHCl$_3$)].

REFERENCE EXAMPLE 21

A 2.5M solution of n-butyllithium in hexane (4.5 ml) was added dropwise to a stirred solution of [2R]-2-methoxymethyl-1-[2-(pyrid-3-yl)cyclohexylideneamino]pyrrolidine (50:50 mixture of diastereoisomers, 2.7 g) in dry tetrahydrofuran (40 ml) at −75° C. under argon during 15 minutes, to give a dark red solution. After 30 minutes, a solution of methyl isothiocyanate (0.8 g) in tetrahydrofuran (8 ml) was added during 10 minutes. The solution was allowed to warm to 0° C. during 45 minutes, maintained at this temperature for 1 hour and then at 20° C. for 1 hour, giving a yellow solution. This solution was quenched with saturated aqueous ammonium chloride solution (20 ml). The organic layer was separated and the aqueous layer extracted with either (3×10 ml). The combined extracts were washed with brine (2×5 ml), dried over magnesium sulphate and evaporated (40° C.; 25 mmHg) to give crude [2R]-anti-2-(methoxymethyl)-1-[2-(pyrid-3-yl)-2-methyl(thiocarbamoyl)cyclohexylideneamino]pyrrolidine, a semi-crystalline oil (3.6 g).

REFERENCE EXAMPLE 22

A mixture of 2-(pyrid-3-yl)cyclohexanone (1.8 g, 1.0 mmol), [R]-(−)-1-amino-2-(methoxymethyl)pyrrolidine ('RAMP') (1.3 g, 1.0 mmol) and p-toluenesulphonic acid (30 mg) was refluxed in toluene (20 ml) for 2.5 hours. The toluene was removed in vacuo to afford an oil which was dissolved in diethylether (30 ml) and washed with aqueous saturated sodium bicarbonate solution (2×15 ml). The organic phase was dried over magnesium sulphate and then filtered and concentrated in vacuo (40° C.; 30 mmHg) to afford [2R,2'R]-2-(methoxymethyl)-1-[2-(pyrid-3-yl)cyclohexylidenamino]pyrrolidine and [2R,2'S]-2-(methoxymethyl)-1-[2-(pyrid-3-yl)cyclohexylideneamino]pyrrolidine (2.72 g) as a 50:50 mixture of diastereoisomers.

REFERENCE EXAMPLE 23 i) A mixture of 2-(pyrid-3-yl)cyclohexanone (60.0 g, 0.34 mole), [R]-1-phenylethylamine (48.6 ml, 0.38 mole) and p-toluenesulphonic acid hydrate (0.6 g) in toluene (480 ml) was refluxed in a Dean-Stark apparatus for 3.5 hours. After cooling the solution was concentrated in vacuo (14 mmHg, 45° C. and then at 0.1 mmHg, 40° C).

The crude 2-(pyrid-3-yl)-1-[R]-1-phenylethylimino]cyclohexane (101.8 g) was dissolved in anhydrous tetrahydrofuran (360 ml) and the resulting solution cooled to −78° C. under argon.

n-Butyllithium (2.5M in hexane; 180 ml, 0.45 mole) was then added dropwise over 45 minutes at −65° C. The mixture was then stirred at −70° C. for a further 30 minutes. A solution of methyl isothiocyanate (33 g, 0.45 mole) in tetrahydrofuran (50 ml) was added to the reaction over 30 minutes at −65° C. After a further 1 hour at −70° C. the mixture was warmed to 20° C. over 40 minutes and then warmed to 30° C. over 10 minutes to afford a semi-solid mass. The mixture was then cooled to 0° C. and aqueous ammonium chloride solution (20% w/w) (600 ml) was added over 15 minutes. The organic phase was removed and the aqueous layer extracted with hexane (300 ml). The combined organic fractions were washed with water (600 ml) and then treated with aqueous acetic acid (40%v/v, 510 ml) at 0° C. The mixture was warmed to 20° C. and stirred for 45 minutes. Concentrated aqueous ammonia solution (33% w/w, 150 ml) was then added at 0° C. and the mixture allowed to stand at 0° C. for 15 hours. The precipitated solid was filtered off, washed with diethyl ether (3×100 ml) and dried at 80° C. to afford the crude product (46.7 g), which was recrystallized from ethyl acetate (2.31) to give [S]-N-methyl-2-oxo-1-(pyrid-3-yl)cyclohexanecarbothioamide (34.5 g, 0.14 mole), m.p. 196°–198° C., $[\alpha]_D^{25} = 84.0$ (c=0.57, CHCl$_3$).

ii) By proceeding in a similar manner but using 1-[R]-(1-naphthyl)ethylamine in place of the 1-[R]-phenylethylamine, [S]-N-methyl-2-oxo-1-(pyrid-3-yl)cyclohexanecarbothioamide was again obtained.

REFERENCE EXAMPLE 24

To a solution of tetrahydropyran-2-yloxyethanonitrile (6.0 g, 42.49 mmol) in ethanol (15 ml) was added aqueous sodium hydroxide solution (10M, 15 ml). Following the initial exothermic reaction the solution was heated under reflux for 1.5 hours, diluted with ethanol (30 ml) and the pH adjusted to 8 by the addition of carbon dioxide pellets. The resulting gelatinous suspension was diluted with acetonitrile (60 ml), filtered at 60° C. through diatomaceous earth and the insoluble material extracted in a similar manner with a mixture of acetonitrile/ethanol/water (4:3:1, 2×120 ml). The crude product was purified by dissolution in warm isopropanol, filtration at 0° C. through diatomaceous earth, evaporation of the solvent in vacuo and trituration of the residue with acetone at 0° C. to yield sodium tetrahydropyran-2-yloxyethanoate (6.24 g, 34.26 mmol) as a colorless powder, m.p. 198°–205° C.;

[Found: C, 45.8; H, 6.1%

Calculated for C$_7$H$_{11}$NaO$_4$: C, 46.2; H, 6.1%].

The present invention includes within its scope pharmaceutical compositions which comprise a compound of general formula (I) or a pharmaceutically acceptable salt thereof, in association with a pharmaceutically acceptable carrier or coating. In clinical practice the compounds of the present invention may be administered rectally, but are preferably administered parenterally, by inhalation if appropriate, or, more preferably, orally.

Solid compositions for oral administration include compressed tablets, pills, powders and granules. In such solid compositions, one or more of the active compounds is, or are, admixed with at least one inert diluent such as starch, sucrose or lactose.

The compositions may also comprise, as is normal practice, additional substances other than inert diluents, e.g. lubricating agents, such as magnesium stearate.

Liquid compositions for oral administration include pharmaceutically acceptable emulsions, inert diluents commonly used in the art such as water and liquid paraffin. Besides inert diluents such compositions may comprise adjuvants, such as wetting, and suspending agents, and sweetening, flavouring, perfuming and preserving agents. The compositions according to the invention for oral administration also include capsules of absorbable material such as gelatin, containing one or more of the active substances with or without the addition of diluents or excipients.

Compositions according to the invention for parenteral administration include sterile aqueous, aqueous-organic, and organic solutions, suspensions and emulsions. Examples of organic solvents or suspending media are propylene glycol, polyethylene glycol, vegetable oils such as olive and injectable organic esters such as ethyl oleate. The compositions may also contain adjuvants such as stabilizing, preserving, wetting, emulsifying and dispersing agents. They may be sterilized by, for example, filtration through a bacteria-retaining filter, by incorporation in the compositions of sterilizing agents, by irradiation or by heating. They may also be manufactured in the form of sterile solid compositions, which can be dissolved in sterile water or some other sterile injectable medium immediately before use.

Compositions for inhalation may be sterile aqueous solutions which are then nebulized or dry powders formulated in accordance with known methods.

Solid compositions for rectal administration include suppositories formulated in accordance with known methods and containing one or more of the compounds of formula (I) or a pharmaceutically acceptable salt thereof.

The percentage of active ingredient in the composition of the invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration, the duration of the treatment and the condition of the patient. In the adult, the doses are generally from 0.001 to 50 mg/kg body weight per day by oral administration. By inhalation, either as a nebulized solution or as a formulated dry powder, the preferred daily dosage is from 0.001 to 5 mg/kg body weight.

The compounds may also be applied topically for inhibition of head hair loss associated with male pattern baldness, the preferred daily dosage being from 0.1 to 10 mg/kg body weight applied, for example, in 5 ml portions two or three times per day.

The following Example illustrates a pharmaceutical composition according to the present invention.

COMPOSITION EXAMPLE

No. 2 size gelatin capsules each containing:

| | |
|---|---|
| (±)-trans-2-Butanoyloxy-N-methyl-1-(pyrid-3-yl)-cyclohexanecarbothioamide | 20 mg |
| Lactose | 100 mg |
| Starch | 60 mg |
| Dextrin | 40 mg |
| Magnesium stearate | 1 mg | were prepared in accordance with the usual procedure.

What is claimed is:

1. Compounds of the formula (I)

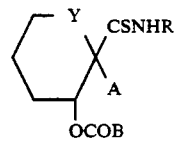

wherein R represents an alkyl group;

A represents a pyrid-3-yl group, optionally substituted by an alkyl or alkoxy group, or a halogen atom;

Y represents
an ethylene or methylene group or a direct bond; and

B represents a phenyl group, or a phenyl group substituted by one or more substituents selected from:
1) halogen atoms;
2) hydroxy, alkyl, C$_{2-4}$-alkenyl, alkoxy, phenoxy, tetrahydropyranyloxy, alkanoyl, benzoyl, cyano, trifluoromethyl, carboxy, amino, (optionally hydroxy)alkylamino, di(optionally hydroxy)alkylamino, trialkylammonio, alkoxycarbonylamino, alkanoylamino, benzoylamino, alkanoyloxy, or alkoxycarbonyl groups;
3) carbamoyl, N-alkylcarbamoyl, N,N-dialkylcarbamoyl, or N-alkylpiperazinocarbonyl groups; and stereoisomers and salts thereof.

2. A compound according to claim 1 in which the —OCOB and CSNHR groups are in the trans configuration.

3. A compound according to claim 1 which is a 1S, 2R enantiomer.

4. A compound according to claim 1, comprising:

B (±)-trans-2-(4-Fluorobenzoyloxy)-N-methyl-1-(pyrid-3-yl)cyclohexanecarbothioamide, D (±)-trans-2-(2-Carboxybenzoyloxy)-N-methyl-1-(pyrid-3-yl)cyclohexanecarbothioamide, G (±)-trans-2-Benzoyloxy-N-methyl-1-(pyrid-3-yl)cyclohexanecarbothioamide, J (±)-cis-2-Benzoyloxy-N-methyl-1-(pyrid-3-yl)cyclohexanecarbothioamide, K [1S,2R]-trans-2-Benzoyloxy-N-methyl-1-(pyrid-3-yl)cyclohexanecarbothioamide, L (±)-trans-N-Methyl-2-(2-methylbenzoyloxy)-1-(pyrid-3-yl)cyclohexanecarbothioamide, M (±)-trans-2-(4-Chlorobenzoyloxy)-N-methyl-1-(pyrid-3-yl)cyclohexanecarbothioamide, N (±)-trans-2-(3-Fluorobenzoyloxy)-N-methyl-1-(pyrid-3-yl)cyclohexanecarbothioamide, O (±)-trans-2-(2-Fluorobenzoyloxy)-N-methyl-1-(pyrid-3-yl)cyclohexanecarbothioamide, P (±)-trans-2-(3,4-Difluorobenzoyloxy)-N-methyl-1-(pyrid-3-yl)cyclohexanecarbothioamide, Q (±)-trans-Methyl-1(pyrid-3-yl)-2-(2-trifluoromethylbenzoyloxy)cyclohexanecarbothioamide, R (±)-trans-N-Methyl-1(pyrid-3-yl)-2-(3-trifluoromethylbenzoyloxy)cyclohexanecarbothioamide, S (±)-trans-N-Methyl-1(pyrid-3-yl)-2-(4-trifluoromethylbenzoyloxy)cyclohexanecarbothioamide, T (±)-trans-2-(3,5-bistrifluoromethylbenzoyloxy)-N-methyl-1-(pyrid-3-yl)cyclohexanecarbothioamide, U (±)-trans-2-(3-Methoxybenzoyloxy)-N-methyl-1-(pyrid-3-yl)cyclohexanecarbothioamide, V (±)-trans-2-(4-Dimethoxybenzoyloxy)-N-methyl-1-(pyrid-3-yl)cyclohexanecarbothioamide, W (±)-trans-N-Methyl-1-(pyrid-3-yl)-2-(3,4,5-trimethoxybenzoyloxy)cyclohexanecarbothioamide, X (±)-trans-2-(4-Methoxybenzoyloxy)-N-methyl-1-(pyrid-3-yl)cyclohexanecarbothioamide, AD [1R,2S]-trans-2-Benzoyloxy-N-methyl-1-(pyrid-3-yl)cyclohexanecarbothioamide, and stereoisomers or salts thereof.

5. The compound [1R,2S]-trans-2-Benzoyloxy-N-methyl-1-(pyrid-3-yl)cyclohexanecarbothioamide.

6. A pharmaceutical composition comprising a thioformamide derivative having the formula (I)

wherein R represents an alkyl group;

A represents a pyrid-3-yl group, optionally substituted by an alkyl or alkoxy group, or a halogen atom;

Y represents:
an ethylene or methylene group or a direct bond; and

B represents a phenyl group, or a phenyl group optionally substituted by one or more substituents selected from:
1) halogen atoms;
2) hydroxy, alkyl, $C_{2-4}$-alkenyl, alkoxy, phenoxy, tetrahydropyranyloxy, alkanoyl, benzoyl, cyano, trifluoromethyl, carboxy, amino, (optionally hydroxy)alkylamino, di(optionally hydroxy)alkylamino, trialkylammonio, alkoxycarbonylamino, alkanoylamino, benzoylamino, alkanoyloxy, or alkoxycarbonyl groups;
3) carbamoyl, N-alkylcarbamoyl, N,N-dialkylcarbamoyl, or N-alkylpiperazinocarbonyl groups; or stereoisomers and salts thereof in association with a pharmaceutically acceptable carrier or coating.

7. A method of treating of smooth muscle disorders in a mammal comprising administering an effective amount of the pharmaceutical composition of claim 6 to a mammal host.

8. A method according to claim 7, wherein the mammal is man.

* * * * *